United States Patent [19]
Kraus et al.

[11] Patent Number: 5,207,692
[45] Date of Patent: May 4, 1993

[54] SURGICAL CLIP APPLIER WITH RECIPROCATING CLIP SLEEVE AND DUAL RATCHET MECHANISM

[75] Inventors: Robert G. Kraus, Attleboro; Philip C. Walker, Cambridge; Herbert H. Loeffler, Arlington; Frederick W. Faller, Burlington; Richard C. Schneider, Framingham; Charles B. Worrick, III, Hanson; Raphael F. Meloul, Brockton, all of Mass.

[73] Assignee: Codman & Shurtleff, Inc., Randolph, Mass.

[21] Appl. No.: 559,751

[22] Filed: Jul. 30, 1990

[51] Int. Cl.$^5$ .............................................. A61B 17/00
[52] U.S. Cl. .................................. 606/143; 606/139; 227/901
[58] Field of Search ............... 606/139, 142, 143, 151, 606/157, 158, 139, 143; 227/901

[56] References Cited

U.S. PATENT DOCUMENTS

| | | | |
|---|---|---|---|
| 3,446,212 | 5/1969 | LeRoy | 606/139 |
| 3,601,127 | 8/1971 | Finegold | 24/263 |
| 3,604,425 | 9/1971 | LeRoy | 24/255 |
| 3,780,416 | 12/1973 | Rider | 29/212 |
| 4,152,920 | 5/1979 | Green | 606/139 |
| 4,217,902 | 8/1980 | March | 606/151 |
| 4,299,224 | 11/1981 | Noiles | 606/139 |
| 4,424,810 | 1/1984 | Jewusiak | 606/158 |
| 4,425,915 | 1/1984 | Ivanov | 606/142 |
| 4,427,008 | 1/1984 | Transue | 606/142 |
| 4,430,997 | 2/1984 | DiGiovanni et al. | 606/142 |
| 4,434,795 | 3/1984 | Mericle | 606/142 |
| 4,450,840 | 5/1984 | Mericle et al. | 606/142 |
| 4,452,376 | 6/1984 | Klieman et al. | 606/142 |
| 4,478,218 | 10/1984 | Mericle | 606/142 |
| 4,509,518 | 4/1985 | McGarry . | |
| 4,522,207 | 6/1985 | Klieman et al. . | |
| 4,534,351 | 8/1985 | Rothfuss et al. . | |
| 4,557,263 | 12/1985 | Green | 606/142 |
| 4,611,595 | 9/1986 | Klieman et al. | 606/142 |
| 4,612,932 | 9/1986 | Caspar et al. | 606/142 |
| 4,616,651 | 10/1986 | Golden . | |
| 4,624,254 | 11/1986 | McGarry et al. . | |
| 4,637,395 | 1/1987 | Caspar et al. | 606/142 |
| 4,638,804 | 1/1987 | Jewusiak | 606/151 |
| 4,671,278 | 6/1987 | Chin | 606/142 |
| 4,674,504 | 6/1987 | Klieman et al. . | |
| 4,791,707 | 12/1988 | Tucker | 606/151 |
| 4,796,627 | 1/1989 | Tucker | 606/151 |
| 4,821,721 | 4/1989 | Chin et al. | 606/139 |
| 4,844,066 | 7/1989 | Stein | 606/157 |
| 4,854,317 | 8/1989 | Braun | 606/139 |

Primary Examiner—Stephen C. Pellegrino
Assistant Examiner—Gary Jackson

[57] ABSTRACT

A surgical clip applier includes a pair of pivotal housing sections on which are provided a pair of clip actuating jaws. An elongated clip sleeve which receives a plurality of surgical clips arranged front to back in a row is mounted for longitudinal reciprocating movement between the housing sections. The clip sleeve includes a pair of clip retaining jaws adjacent to its open front to receive and hold a surgical clip advanced from the clip sleeve between the clip actuating jaws on the housing sections. A pusher is mounted on the clip sleeve for engaging the rearmost clip in the row. The surgical clip applier includes a ratchet mechanism which is operable each time the clip sleeve is reciprocated to advance the pusher and the row of clips by one step corresponding to the length of one surgical clip in the row. The ratchet mechanism includes a first ratchet on the clip sleeve and a second ratchet on one of the housing sections which are engaged by pawls on opposite sides of the pusher. The surgical clip applier operates by a double pump action in which the housing sections are twice pivoted together and released. In the first pump action, the clip sleeve is reciprocated to load the frontmost surgical clip between the clip retaining jaws and to advance the surgical clip to a load position between the clip actuating jaws. In the second pump action, the clip actuating jaws are pivoted into engagement with the clip retaining jaws to actuate the surgical clip held by the clip retaining jaws.

24 Claims, 10 Drawing Sheets

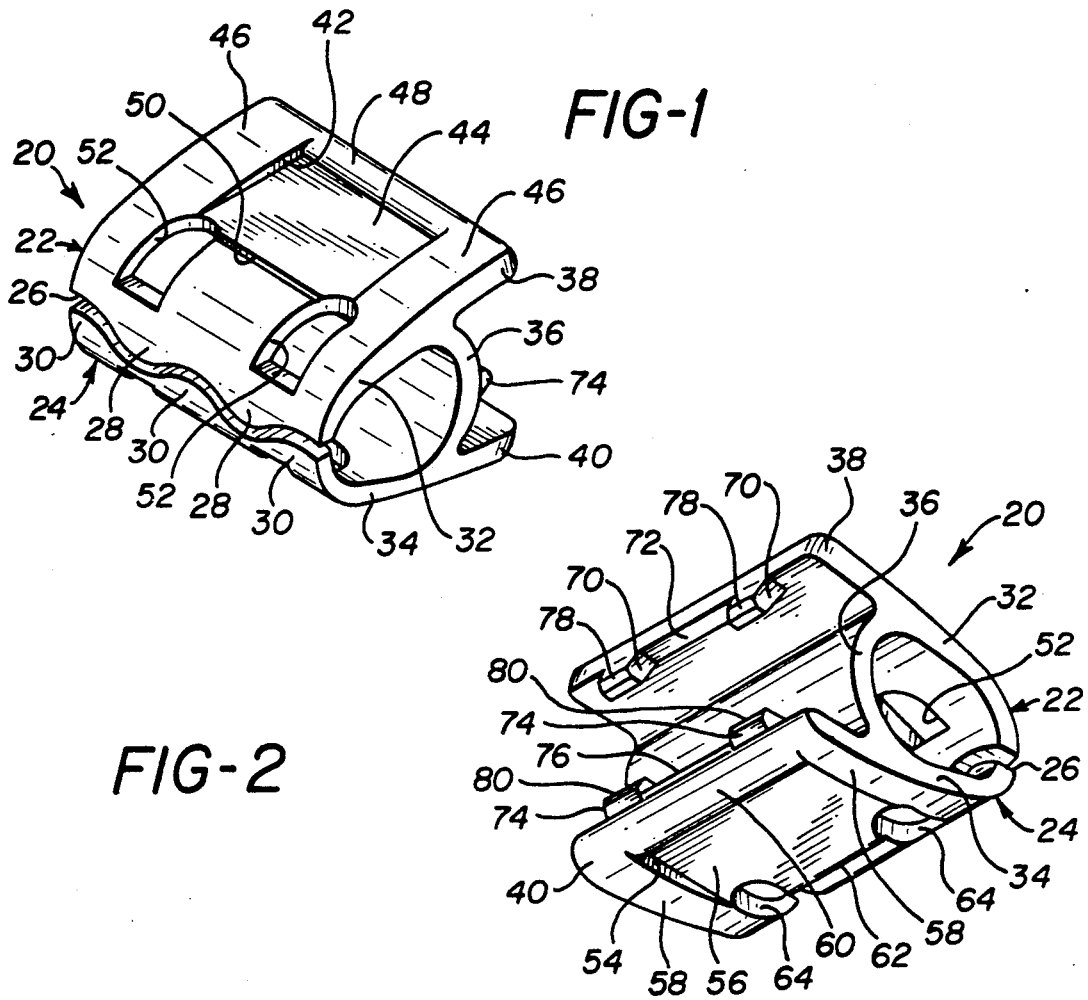
FIG-1
FIG-2
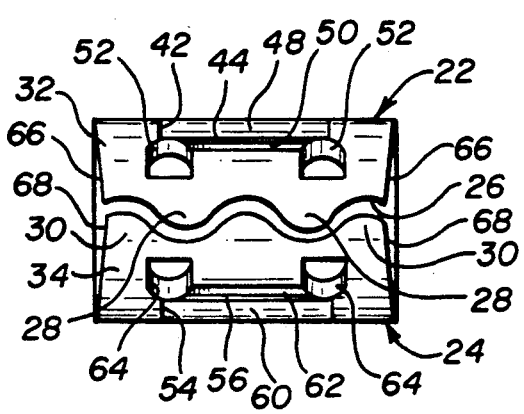
FIG-3
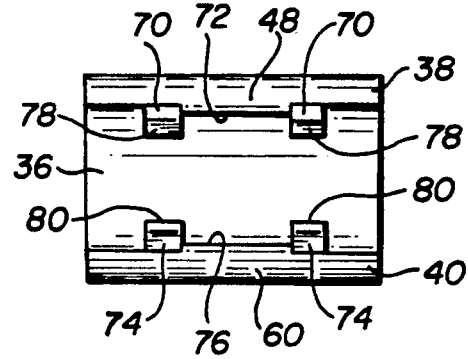
FIG-4

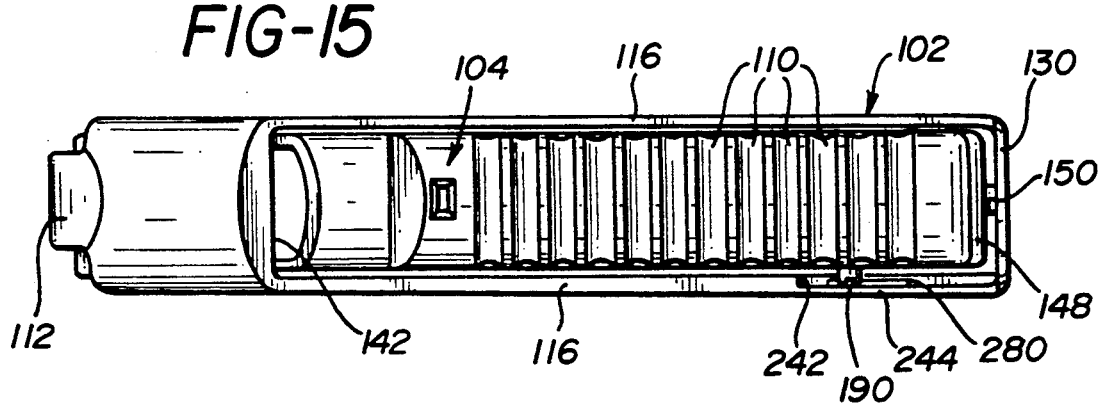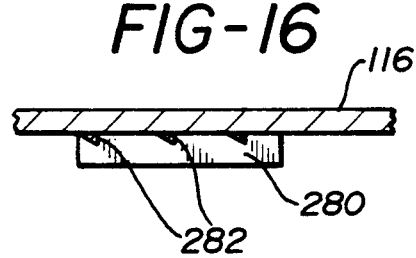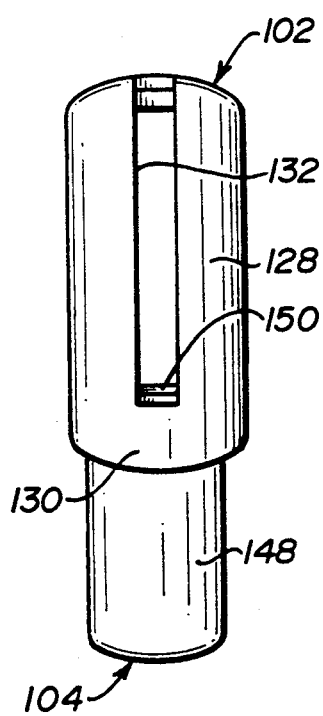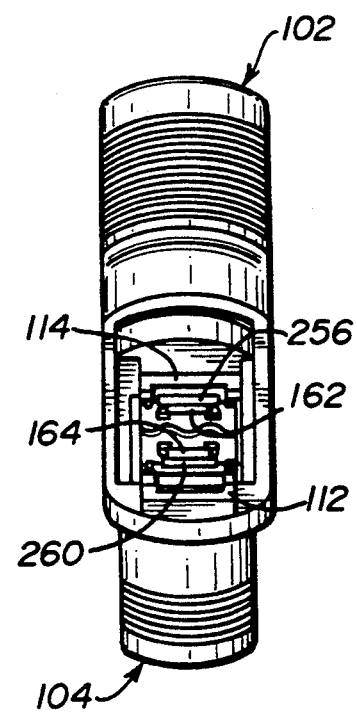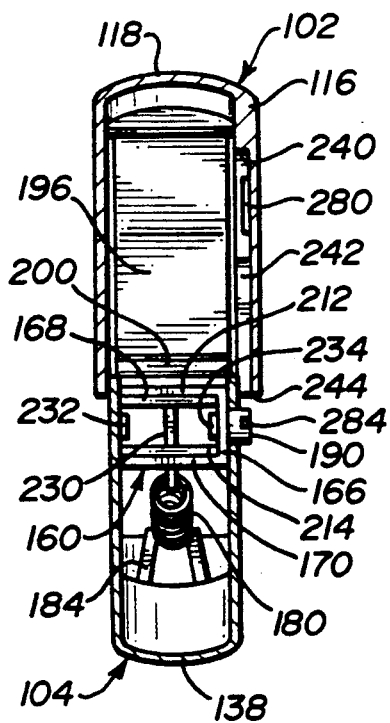

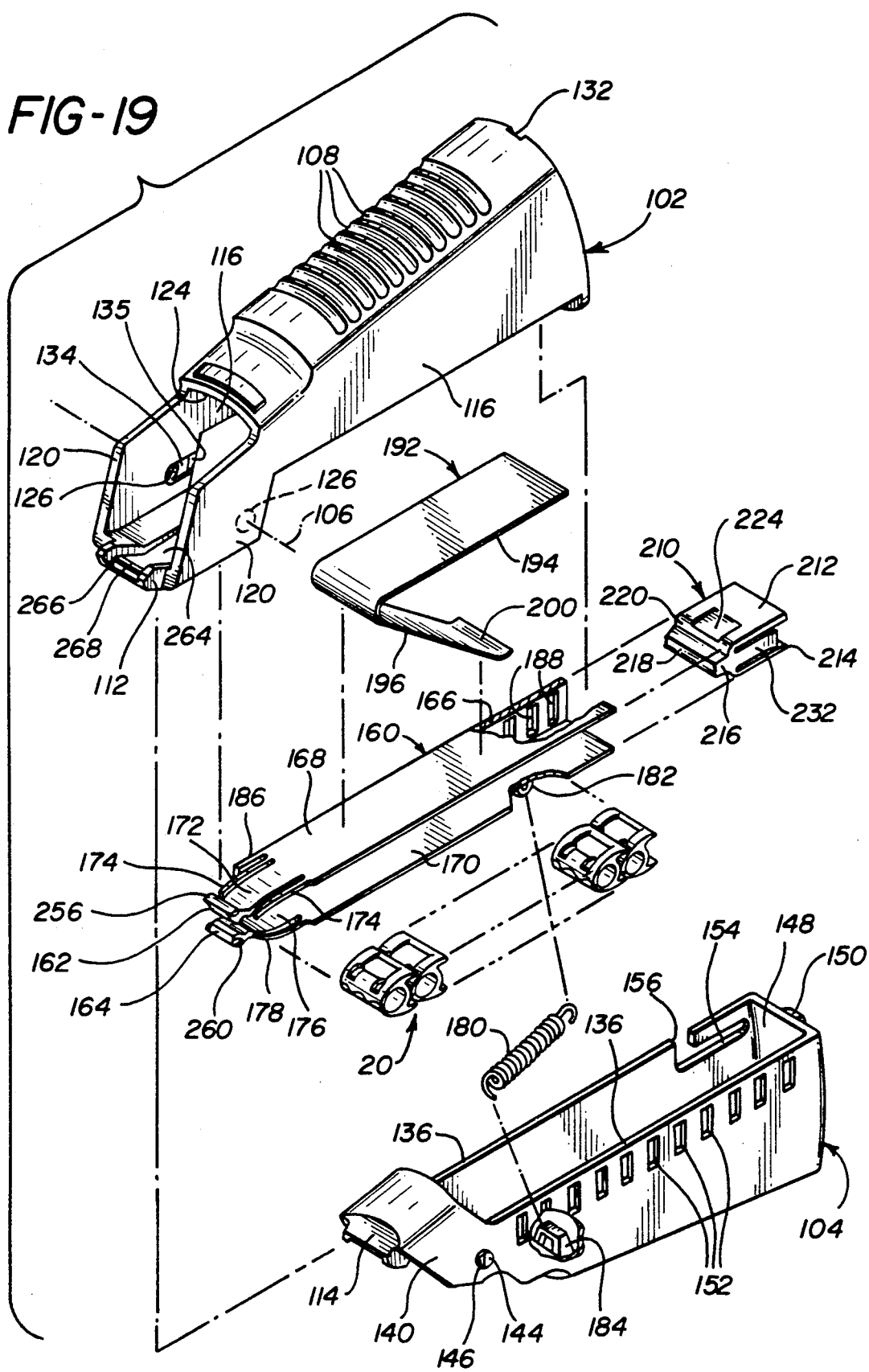

FIG-29
FIG-30
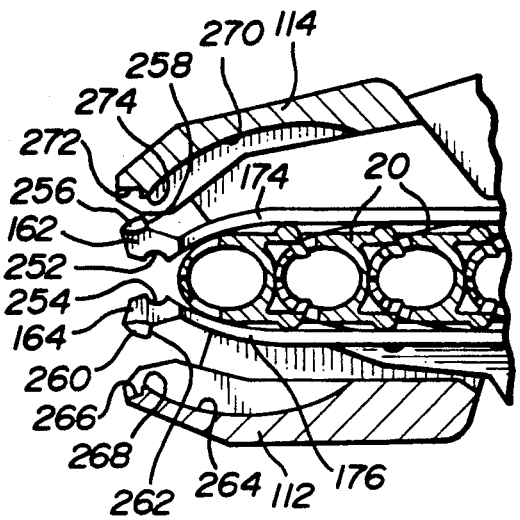
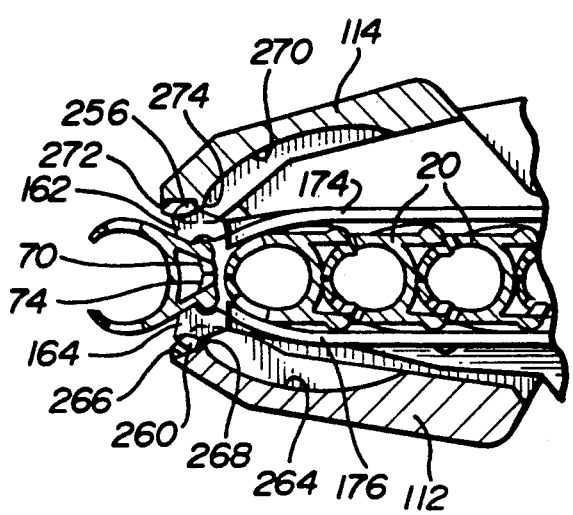
FIG-31
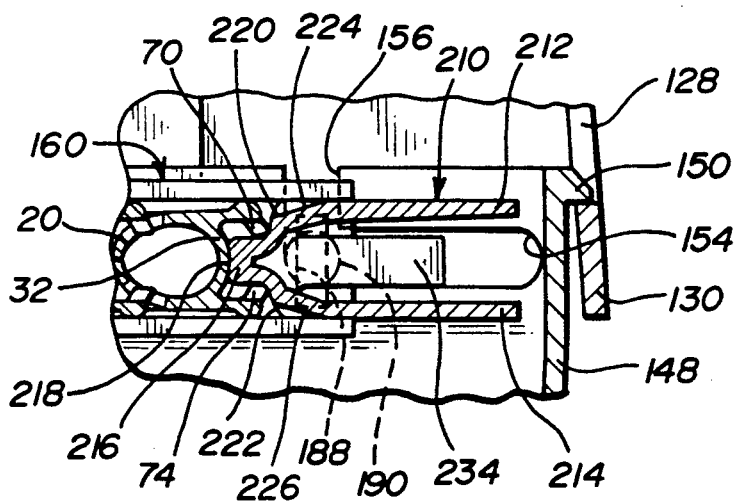
FIG-32
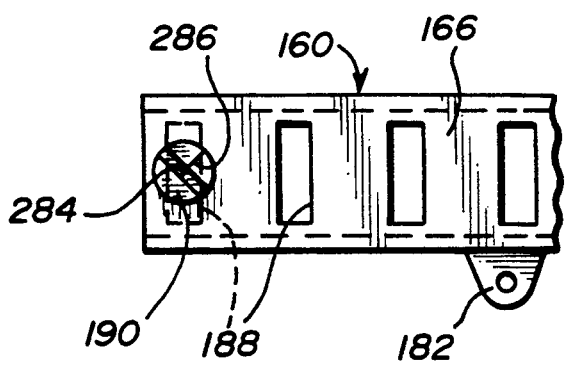
FIG-33
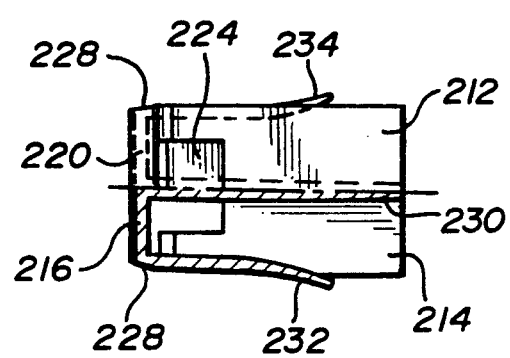

SURGICAL CLIP APPLIER WITH RECIPROCATING CLIP SLEEVE AND DUAL RATCHET MECHANISM

BACKGROUND OF THE INVENTION

1. Field of the Invention

The present invention generally relates to surgical or scalp clips and to a surgical clip applier for applying such clips to human tissue. More particulary, this invention relates to a hemostatic clip which is suitable for use as a scalp clip in the course of cranial surgery and to a surgical clip applier for repeatedly advancing scalp clips one at a time from a clip sleeve or magazine and applying the scalp clips to a tissue wound flap.

2. Description of the Prior Art

In the prior art, hemostatic clips are known for use in clamping wound flaps to prevent the flow of blood from severed blood vessels. For example, U.S. Pat. No. 3,604,425 discloses a hemostatic clip in the form of a tubular body member having a longitudinal slit extending completely across the body for receiving a wound flap when the body is distended from its original shape. A pair of outwardly extending projections is connected to the clip body at positions remote from the slit for accommodating a force applying tool. When force is applied to the outwardly extending projections, the clip body is distended from its original tubular shape to widen the slit and permit the insertion of a wound flap therein. When the force is released, the clip body returns to its original undistended tubular shape to clamp the wound flap. The clips are loaded by hand one at a time into a forceps-like tool for application to the wound flap.

The configuration of the hemostatic clip disclosed in U.S. Pat. No. 3,604,425 is unsuitable for use with a clip applying instrument in which a plurality of clips are loaded in a magazine and advanced one at a time to a set of clip actuating jaws. Because of the shape of the clip body and location of the outwardly extending projections on the clip body, it is difficult to maintain a series of such clips in alignment within a clip magazine. When the clips are arranged front to back in a row, there is a tendency of the clips to rotate relative to each other and to become misaligned. In view of these problems, it would be difficult to feed such hemostatic clips one at a time from a clip magazine and to accurately align the clips with the jaws of the clip applying instrument.

Accordingly, it is desirable to provide a surgical clip, such as a scalp clip, with a configuration which is readily operable with an applicator for applying a series of such clips to a wound flap. Also, it is desirable to provide a surgical or scalp clip with a configuration that permits a plurality of such clips to be loaded into a clip sleeve or magazine of an applicator for applying the clips to tissue. Further, it would be advantageous to provide a surgical or scalp clip with a configuration that maintains the clips in alignment when arranged front to back in a row within a clip sleeve or magazine and which prevents the clips from rotating with respect to each other in the clip sleeve or magazine. Further, it is desirable to design the surgical or scalp clip to limit the maximum separation of its clamping jaws when the clip body is distended by the applicator.

It has been proposed to provide a scalp clip applicator for applying a plurality of scalp clips one after the other without having to insert an individual scalp clip into the applicator after each application. U.S. Pat. No. 4,637,395 discloses an applicator for C-shaped scalp clips provided with a magazine for receiving a plurality of scalp clips arranged one behind the other with the free ends of one scalp clip resting against the bridge of the adjacent scalp clip. The scalp clips are urged forwardly along the magazine by a spirally wound leaf spring attached to a slider which engages the rearmost scalp clip. The frontmost clip engages the applicator jaws at the front of the magazine. Each scalp clip has laterally projecting edges to which force is applied by the applicator jaws to open the clamping jaws of the scalp clip to receive a layer of tissue. When the force is released, the clamping jaws of the scalp clip close to clamp the tissue.

In a first embodiment of the scalp clip applicator of U.S. Pat. No. 4,637,395, all clips in the magazine are advanced when the frontmost clip is released from the applicator jaws. No provision is made to retain the next scalp clip safely inside the magazine until the surgeon desires to operate the applicator to apply the next scalp clip to a tissue flap. Also, no provision is made to prevent the remaining clips in the magazine from pushing against the frontmost clip when it is actuated by the applicator jaws. As a result, the leading clip may become misaligned or accidently dislodged from the applicator jaws.

In a second embodiment of the scalp clip applicator of U.S. Pat. No. 4,637,395, a retaining nose projects downwardly into the feed path of the scalp clips to engage the second clip in the magazine. The purpose of the retaining nose is to prevent the second clip and the remaining clips from being pushed against the leading clip. However, when the lower applicator jaw is activated to open the leading clip, the retaining nose is raised so that the clips are pushed against the leading clip while it is being actuated by the applicator. As a result, the leading clip may become misaligned or dislodged from the applicator jaws. Also, in both embodiments, no provision is made to prevent the scalp clips from rotating with respect to each other so that the clips may become misaligned in the magazine.

U.S. Pat. No. 4,821,721 discloses a device for applying LeRoy-Raney clips in which a plurality of clips is loaded vertically in a magazine. The clip at the top of the magazine is driven laterally by a plunger through a tapered tunnel which forces the clip jaws open to allow the clip to be applied to a scalp edge at the end of the tunnel. However, no provision is made to maintain the scalp clips in alignment within the magazine and no provision is made to prevent the scalp clips from rotating with respect to each other in the magazine.

U.S. Pat. No. 4,674,504 discloses a clip applying device with a clip magazine including a double ratchet mechanism comprising two ratchet bars coupled to a pawl for advancing hemostatic clips through the magazine. A separate feed blade is slidably received in the magazine and used to advance the leading clip from the magazine to the applier jaws. The leading clip is moved sideways in front of the feed blade prior to its advancement to the applier jaws. The magazine is stationary and one of the ratchet bars is reciprocated by the feed blade to advance the clips from the magazine to the applier jaws.

Accordingly, it is desirable to provide a surgical clip applier including a clip sleeve or magazine in which a plurality of surgical clips is maintained in accurate alignment and the clips are advanced one at a time to a set of clip actuating jaws. Also, it is desirable to provide a surgical clip applicator which advances a plurality of surgical clips one at a time from a clip sleeve or magazine and safely retains the remaining clips within the magazine and out of engagement with the leading clip. Further, it is desirable to provide a surgical clip applicator which precludes the premature advance of another surgical or scalp clip from the clip sleeve or magazine until the application of the previous surgical clip to a tissue flap is completed.

A preferred embodiment of the surgical clip comprises a body in the form of an elongated tubular element having an ellipsoidal cross section. The surgical clip includes wound flap engaging means comprising a pair of tissue clamping jaws defined by an elongated longitudinal slit extending completely across the front of the body. The tissue clamping jaws are connected by a flexible bridge at the rear of the body whereby the body may be distended from its original tubular shape. A pair of flanges extend rearwardly from opposite sides of the body at positions remote from the longitudinal slit. The flanges are adapted to engage the jaws of an applier whereby pressure can be applied to the bridge via the flanges to widen the slit and separate the tissue clamping jaws to permit a tissue flap to be inserted therebetween. The body is resiliently urged by the bridge to maintain its original tubular shape whereby the tissue clamping jaws will engage the tissue flap when the pressure applied to the flanges by the applier is released. Jaw guide means is formed on opposite sides of the body for receiving and guiding the jaws of the applier into engagement with the flanges.

Preferably, the flanges include a pair of elongated ridges extending across the rear of the flanges for engaging the jaws of the applier. The guide means comprises a pair of indentations formed on opposite sides of the clip body which extend rearwardly into the flanges and terminate at the ridges. The indentations define a pair of recessed, flat surfaces on opposite sides of the clip body which extend rearwardly into the flanges. Each of the flat surfaces is flanked by a pair of ramp-like surfaces extending along the opposite edges of the body. The recessed, flat surfaces receive and guide the applier jaws between the ramp-like surfaces to the ridges at the rear of the flanges on the clip body.

According to another aspect of the invention, the surgical clip is provided with stop means on its rearwardly extending flanges for limiting the separation of the tissue clamping jaws when the clip body is distended by the pressure applied to the flanges. Preferably, one or more tabs is formed on the inside of each flange and the tabs on each flange are aligned with the corresponding tabs on the opposite flange. The tabs are adapted to engage each other when the body is distended to limit the maximum separation of the tissue clamping jaws. In addition, one or more notches is formed at the front of the clip body on each of the tissue clamping jaws for receiving the corresponding tabs on the flanges of another surgical clip to maintain the clips in alignment when arranged front to back in a row.

According to another aspect of the invention, the surgical clip includes shoulder means on the opposite sides of the clip body for engaging the rearwardly extending flanges of another surgical clip to maintain the clips in alignment and prevent rotation of the clips when arranged front to back in a row. Preferably, the surgical clip includes a pair of shoulders formed at the front of its tissue clamping jaws and a pair of ledges formed on the inside of its flanges. In a row of surgical clips arranged front to back, the shoulders of each surgical clip engage the ledges of another surgical clip to maintain the clips in alignment and prevent the surgical clips from rotating with respect to each other.

SUMMARY OF THE INVENTION

The present invention achieves a surgical clip and surgical clip applier which are particularly suitable for applying a series of surgical clips from a clip sleeve or magazine to a tissue flap. The surgical clip applier includes a reciprocating magazine and a ratchet mechanism for advancing the surgical clips one at a time outward from an open front end of the clip sleeve. The applier includes a set of clip retaining jaws on the clip sleeve for engaging and holding the frontmost surgical clip when it is advanced from the clip sleeve. The applier also includes a set of clip actuating jaws for actuating the clip retaining jaws to open and close the surgical clip held by the clip retaining jaws. The surgical clip is designed to align itself with the other surgical clips arranged front to back in the clip sleeve and to prevent the clips from rotation relative to each other. In addition, the configuration of the surgical clip facilitates the loading and operation of the clips by the clip retaining jaws of the surgical clip applier.

In accordance with the invention, the surgical clip applier includes an elongated clip sleeve adapted to receive a plurality of surgical clips arranged front to back in a row and mounted for longitudinal reciprocating movement relative to the applier housing. A pusher is mounted on the clip sleeve for engaging the rearmost clip in the row and is movable one step at a time along the clip sleeve to advance the row of clips toward an open front end of the clip sleeve. The surgical clip applier includes ratchet means operable each time the clip sleeve is reciprocated for advancing the pusher and the row of clips by one step along the clip sleeve, each step corresponding to the length of one clip in the row. In addition, the surgical clip applier includes means for reciprocating the clip sleeve relative to the housing to advance the row of clips toward the front end of the clip sleeve and to move the frontmost clip in the row outward from the front end of the clip sleeve.

Preferably, the surgical clip applier includes a set of clip retaining jaws on the clip sleeve for engaging and holding the frontmost surgical clip when the surgical clip is moved outward from the clip sleeve. Jaw actuating means is provided on the housing for actuating the clip retaining jaws to open and close the surgical clip held by the clip retaining jaws. Clip retaining means is provided at the front end of the clip sleeve for engaging the next surgical clip in the row when the frontmost clip is advanced and held by the clip retaining jaws to retain the remaining surgical clips within the clip sleeve and out of engagement with the frontmost clip.

A preferred embodiment of the surgical clip applier includes a housing comprising first and second housing sections mounted together for pivotal movement about a pivot axis, each housing section having a front portion extending forwardly beyond the pivot axis to form a clip actuating jaw. An elongated clip sleeve is adapted to receive a plurality of surgical clips arranged front to back in a row and mounted for longitudinal reciprocating movement relative to the housing between a forward position and a retracted position. The clip sleeve includes a pair of clip retaining jaws adjacent to an open front end of the clip sleeve and positioned between the clip actuating jaws with the clip sleeve located in the forward position. A pusher is mounted on the clip sleeve for engaging the rearmost clip in the row. The pusher is movable one step at a time along the clip sleeve to advance the row of clips toward the open front end of the clip sleeve.

The preferred embodiment of the surgical clip applier includes ratchet means operable each time the clip sleeve is reciprocated for advancing the pusher and the row of clips by one step along the clip sleeve, each step corresponding to the length of one surgical clip in the row. The ratchet means is embodied as a first ratchet mechanism operable when the clip sleeve is retracted for advancing the pusher and the row of surgical clips by one step relative to the clip sleeve and a second ratchet mechanism operable when the clip sleeve is advanced for advancing the pusher and the row of surgical clips by one step relative to the housing. The first ratchet mechanism includes a first pawl formed on the pusher for engaging a plurality of slots formed on the housing. The second ratchet mechanism includes a second pawl formed on the pusher for engaging a plurality of slots formed on the clip sleeve. Preferably, the first and second pawls are located on opposite sides of the pusher. The slots formed on the housing and on the clip sleeve are uniformly spaced apart by a distance equal to the length occupied by one surgical clip in the row.

In addition, the preferred embodiment of the surgical clip applier includes cam means operable when the housing sections are pivoted together for a first time without a surgical clip between the clip retaining jaws for reciprocating the clip sleeve longitudinally relative to the housing between a forward position and a retracted position. Preferably, the cam means comprises a cam follower on the clip sleeve and a cam surface formed on one of the housing sections which is oriented to engage the cam follower when the housing sections are pivoted together to retract the clip sleeve into the housing. The clip retaining jaws engage the frontmost clip in the row as the clip sleeve is moved to its retracted position and advance the frontmost clip between the clip actuating jaws as the clip sleeve is moved to its forward position. The clip actuating jaws engage the clip retaining jaws when the housing sections are pivoted together for a second time with a surgical clip between the clip retaining jaws to actuate the surgical clip to receive a tissue flap therein.

According to another aspect of the invention, the surgical clip applier includes stop means on the clip actuating jaws for engaging the clip retaining jaws when the housing sections are pivoted together with a surgical clip held by the clip retaining jaws to maintain the clip sleeve in its forward position. The stop means serves as a reload prevention feature which prevents the clip sleeve from being retracted into the applier housing until the surgical clip held by the clip retaining jaws is released.

According to another aspect of the invention, the surgical clip applier includes latch means for retaining the housing sections pivoted together as the cam surface is moved along the cam follower to prevent the housing sections from pivoting apart until the clip sleeve is fully retracted to load the frontmost clip between the clip retaining jaws. Preferably, the latch means includes a guide rail on one housing section extending parallel to the cam surface, a slot formed in the cam follower for receiving the guide rail as the cam surface is moved along the cam follower, and a set of ratchet teeth formed on the one housing section between the cam surface and the guide rail. A lip formed on the cam follower engages the ratchet teeth as the cam surface is moved along the cam follower to prevent the cam follower from being disengaged from the guide rail until the clip sleeve is fully retracted.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view showing the front and top of a surgical clip embodying the principles of the present invention;

FIG. 2 is a perspective view showing the rear and bottom of the surgical clip of FIG. 1;

FIG. 3 is a front view of the surgical clip;

FIG. 4 is a rear view of the surgical clip;

FIG. 12 is a rear view of the surgical clip applier of FIG. 11;

FIG. 15 is a bottom view of the surgical clip applier;

FIG. 16 is an enlarged section taken along line 16—16 of FIG. 13;

FIG. 17 is a front end view of the surgical clip applier;

FIG. 18 is a vertical section of the surgical clip applier taken along line 18—18 of FIG. 14;

FIG. 19 is an assembly perspective view showing the housing sections, clip sleeve and pusher of the surgical clip applier;

FIG. 29 is an enlarged cutaway elevation of the clip retaining jaws and the clip actuating jaws at the front of the surgical clip applier;

FIG. 30 is an enlarged cutaway elevation of the clip retaining jaws and the clip acutating jaws at the front of the surgical clip applier showing the clip spread fully apart;

FIG. 31 is an enlarged vertical section of a rear portion of the clip sleeve and pusher;

FIG. 32 is an enlarged side elevation showing a cylindrical boss on the opposite side of the clip sleeve; and FIG. 33 is an enlarged partially cutaway top view of the pusher.

DETAILED DESCRIPTION OF PREFERRED EMBODIMENT

Figure 5:
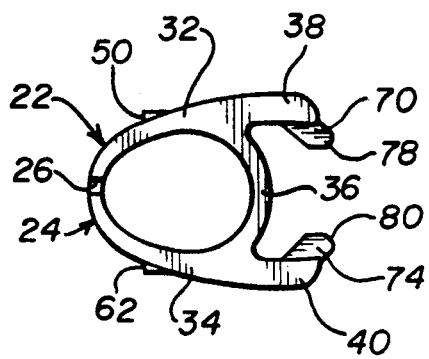
FIG. 5 is a side elevation of the surgical clip of FIG. 1.

Referring to FIG. 1, the present invention is embodied in a surgical clip, generally 20, which is used as a scalp clip in the course of surgery on human tissue. The invention is also embodied in a surgical clip applier, generally 100, shown in FIG. 11, which is particularly adapted for use with the surgical clip 20. The surgical clip 20 may be operated by a conventional clip applier, e.g., a forceps removal tool, or by the surgical clip applier 100 of this disclosure. Although the surgical clips 20 and the surgical clip applier 100 disclosed herein are particularly suitable for the clamping of a tissue flap resulting from an incision made in the scalp of a patient during cranial surgery, it will be understood that the principles of this invention are not limited to scalp clip appliers and scalp clips but may be employed in surgical clip applicators and surgical clips used for other purposes.

As shown in FIGS. 1 and 2, a preferred embodiment of the surgical clip 20 comprises a body in the form of an elongated tubular element having an ellipsoidal cross section. Preferably, the surgical clip 20 comprises a one-piece molded plastic body consisting of a resilient polymer material.

The surgical clip 20 includes wound flap engaging means comprising a pair of tissue clamping jaws 22 and 24 which are defined by an elongated longitudinal slit 26 extending completely across the front of the surgical clip body. Preferably, the longitudinal slit 26 follows a sinusoidal path and defines an upper set of teeth 28 on jaw 22 and a lower set of teeth 30 on jaw 24 which intermesh with each other. As shown in FIG. 1, the upper tissue clamping jaw 22 is formed by an upper wall 32 which slopes downwardly toward the front of the surgical clip body. Similarly, the lower tissue clamping jaw 24 is formed by a lower wall 34 which slopes upwardly toward the front of the surgical clip body. The front portions of upper wall 32 and lower wall 34 curve inwardly and terminate at the edges of the sinusoidal slot 26 which define the teeth 28 and 30, respectively.

The tissue clamping jaws 22 and 24 are connected by a flexible bridge 36 at the rear of the surgical clip body which permits the surgical clip body to be distended from its original tubular shape to open the tissue clamping jaws 22 and 24 to receive a tissue flap therebetween. The surgical clip body is resiliently urged by the bridge 36 to maintain its original tubular shape. A pair of rearwardly extending projections or flanges 38 and 40 are connected to opposite sides of the bridge 36 of the surgical clip body at positions remote from the longitudinal slit 26. The flanges 38 and 40 each extend transversely across the full width of the surgical clip body and smoothly follow the contour of the upper wall 32 and the lower wall 34 of the clip body.

As shown in FIG. 5, the upper wall 32 and the lower wall 34 of the surgical clip 20 are flared rearwardly to form the rear projections or flanges 38 and 40. The upper wall 32 has a large radius of curvature and blends with the front of the upper jaw 22 which is curved more sharply inward toward the horizontal centerline of the surgical clip 20. The top of the flange 38 has the same radius of curvature as the upper wall 32 and the end of the flange 38 is more sharply rounded. Similarly, the lower wall 34 has a large radius of curvature and blends with the front of the lower jaw 24 which is curved more sharply inward toward the horizontal centerline of the surgical clip 20. The bottom of the flange 40 has the same radius of curvature as the lower wall 34 and the end of the flange 40 is more sharply rounded.

Preferably, the surgical clip 20 has smoothly contoured surfaces to avoid slagging with the sutures used in the course of cranial surgery As shown in FIG. 5, the flanges 38 and 40 blend smoothly with the upper wall 32 and the lower wall 34 of the clip body and the rear edges of the flanges 38 and 40 are rounded. Also, the upper flange 38 has rounded corners 45 (FIG. 6) and the lower flange 40 has similarly rounded corners.

Figure 7:
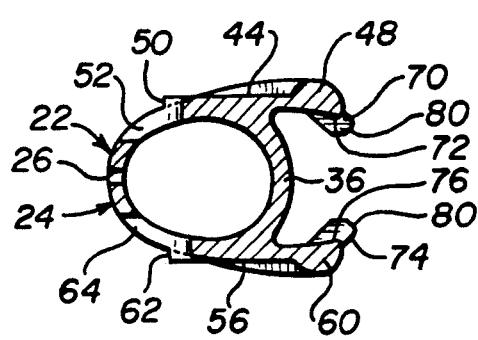
FIG. 7 is a vertical section of the surgical clip taken along line 7—7 of FIG. 6.

Referring to FIG. 1, a wide, centrally located indentation 42 is provided in the upper wall 32 and flange 38 of the surgical clip 20. The indentation 42 provides a flat, recessed surface 44 flanked on opposite sides by a pair of ramp-like surfaces 46. Preferably, as shown in FIG. 7, the flat surface 44 is oriented horizontally or sloped upwardly, front to back, at a slight angle, e.g., 0 degrees, 30 minutes, to the horizontal centerline of the surgical clip 20. The rear portion of flat surface 44 terminates at a ridge 48 which extends transversely across the back of flange 38. The front portion of flat surface 44 terminates at the top of a shoulder 50 which projects outwardly from the upper wall 32 of the surgical clip 20. The shoulder 50 is elongated and extends between a pair of notches 52 (FIG. 3) formed in the upper tissue clamping jaw 22.

Similarly, as shown in FIG. 2, a wide centrally located indentation 54 is formed in the lower wall 34 and flange 40 of the surgical clip 20. The indentation 54 provides a flat, recessed surface 56 flanked on opposite sides by a pair of ramp-like surfaces 58. Preferably, as shown in FIG. 7, the flat surface 56 is oriented horizontally or sloped downwardly, front to back, at a slight angle, e.g., 0 degrees, 30 minutes, to the horizontal centerline of the surgical clip 20. The rear portion of flat surface 56 terminates at a ridge 60 which extends transversely across the back of flange 40. The front portion of flat surface 56 terminates at the top of a shoulder 62 which projects outwardly from the lower wall 34 of the surgical clip 20. The shoulder 62 is elongated and extends between a pair of notches 64 (FIG. 3) formed in the lower tissue clamping jaw 24.

Figure 6:
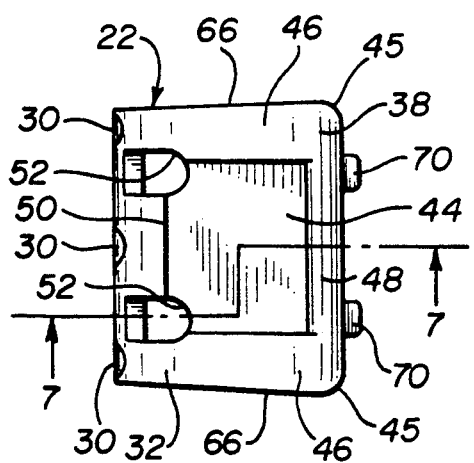
FIG. 6 is a top view of the surgical clip.

As shown in FIGS. 3 and 6, the upper wall 32 has its outer edges 66 tapered inwardly toward the front of the surgical clip body. Also, the lower wall 34 has its outer edges 68 tapered inwardly toward the front of the surgical clip body. Preferably, the outer edges 66 and 68 are tapered at an angle of 1 degree relative to the horizontal centerline of the surgical clip 20.

Referring to FIG. 7, the ridges 48 and 60 at the back of flanges 38 and 40, respectively, are formed with a semi-cylindrical shape to receive the jaws of an applier, e.g., a pair of forceps or the surgical clip applier 100 disclosed herewith When pressure is applied to the ridges 48 and 60 by the forceps or other applier, the pressure is applied via flanges 38 and 40 to the surgical clip body on opposite sides of the bridge 36 to widen the slit 26 and separate the tissue clamping jaws 22 and 24 to permit the insertion of a tissue flap therein. When the pressure applied to the ridges 48 and 60 by the forceps or other applier is released, the bridge 36 returns the surgical clip body to its original tubular shape so that the tissue clamping jaws 22 and 24 engage the tissue flap.

In the preferred embodiment of the surgical clip 20, the bridge 36 has a thickness between 0.039 inch and 0.041 inch. The preferred thickness is 0.040 inch. The thickness is selected to permit the bridge 36 to act as a fulcrum for the flanges 38 and 40 when pressure is applied to the ridges 48 and 60 to open the tissue clamping jaws 22 and 24. Also, the bridge thickness is selected to avoid undesirable distortion of the bridge 36 when the tissue clamping jaws 22 and 24 are opened.

Figure 8:
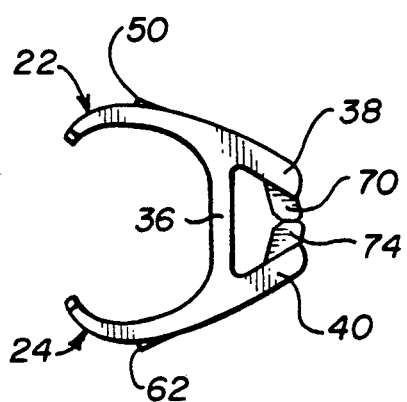
FIG. 8 is a side elevation of the surgical clip with its jaws fully open.

Referring to FIGS. 2 and 4-6, a pair of rear legs or tabs 70 is spaced apart on the inside of flange 38. The legs or tabs 70 slope downwardly and rearwardly from flange 38. A raised ledge 72 on the inside of flange 38 extends transversely between the legs or tabs 70. Similarly, a pair of rear legs or tabs 74 is spaced apart on the inside of flange 40. The legs or tabs 74 slope upwardly and rearwardly from the flange 40. A raised ledge 76 on the inside of flange 40 extends transversely between the legs or tabs 74. The upper tabs 70 each include a tab engaging ledge 78. Similarly, the lower tabs 74 each includes a tab engaging ledge 80. When the body of the surgical clip 20 is distended (FIG. 8), the tab engaging ledges 78 and 80 on the upper tabs 70 and lower tabs 74, respectively, are moved into engagement to limit the maximum separation of the tissue clamping jaws 22 and 24.

Figure 9:
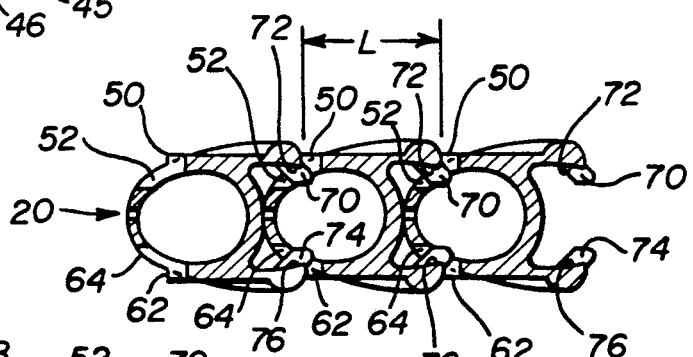
FIG. 9 is a partially cutaway side elevation showing a plurality of surgical clips arranged front to back in a row.
Figure 10:
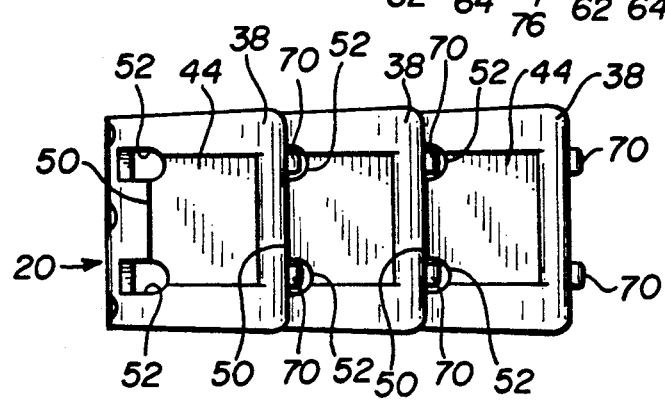
FIG. 10 is a top view showing a plurality of surgical clips arranged front to back in a row.

As shown in FIG. 9, a plurality of surgical clips 20 can be arranged back to back in a row within a clip sleeve or magazine of a surgical clip applier. With the surgical clips 20 arranged front to back, the front shoulders 50 and 62 of each surgical clip 20 engage the flanges 38 and 40 and the rear ledges 72 and 76 on the next surgical clip 20 to maintain the surgical clips 20 uniformly spaced apart in a straight line and to prevent relative rotation between adjacent surgical clips 20 in the row. Also, as shown in FIG. 10, the front notches 52 and 64 of each surgical clip 20 receive the rear tabs 70 and 74 of the previous surgical clip 20 in the row to limit the lateral movement and to prevent relative rotation between the adjacent surgical clips 20 in the row. As a result, the surgical clips 20 are accurately aligned front to back in a straight line and all axial rotation, i.e., roll, pitch and yaw, is effectively precluded between adjacent clips in the row. The horizontal distance between the front of the shoulders 50 and 62 and the rear of the ledges 72 and 76 represents the stack length "L" (FIG. 9) occupied by one surgical clip 20 when a row or stack of surgical clips 20 is arranged front to back within a clip sleeve or magazine.

Figure 11:
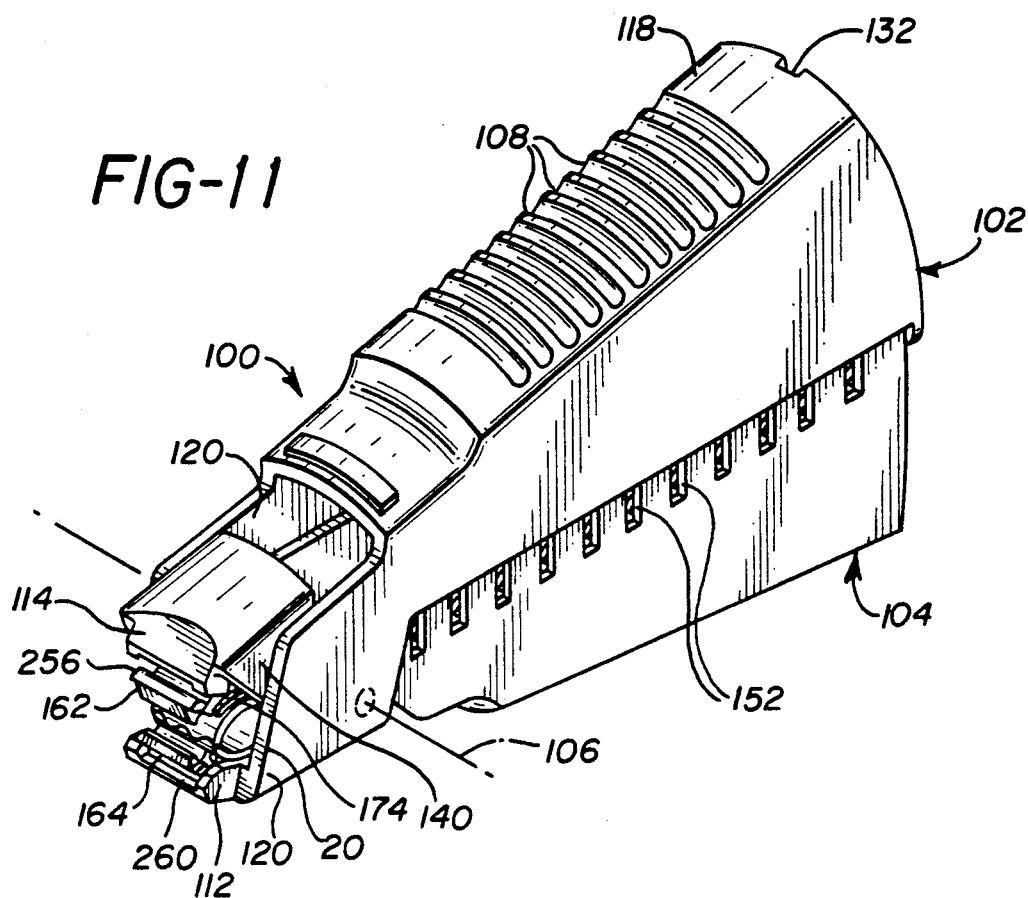
FIG. 11 is a perspective view showing the front and one side of a surgical clip applier embodying the principles of the present invention.

Referring to FIG. 11, the present invention is embodied in a surgical clip applier, generally 100, for applying a series of surgical clips, such as scalp clips, in the course of surgery on human tissue. Although the surgical clips 20 and the surgical clip applier 100 of this disclosure are particularly suitable for the clamping of a tissue flap resulting from an incision made in the scalp of a patient during cranial surgery, it will be understood that the principles of this invention are not limited to scalp clip appliers and scalp clips but may be employed in surgical clip applicators and surgical clips used for other purposes.

Figure 13:
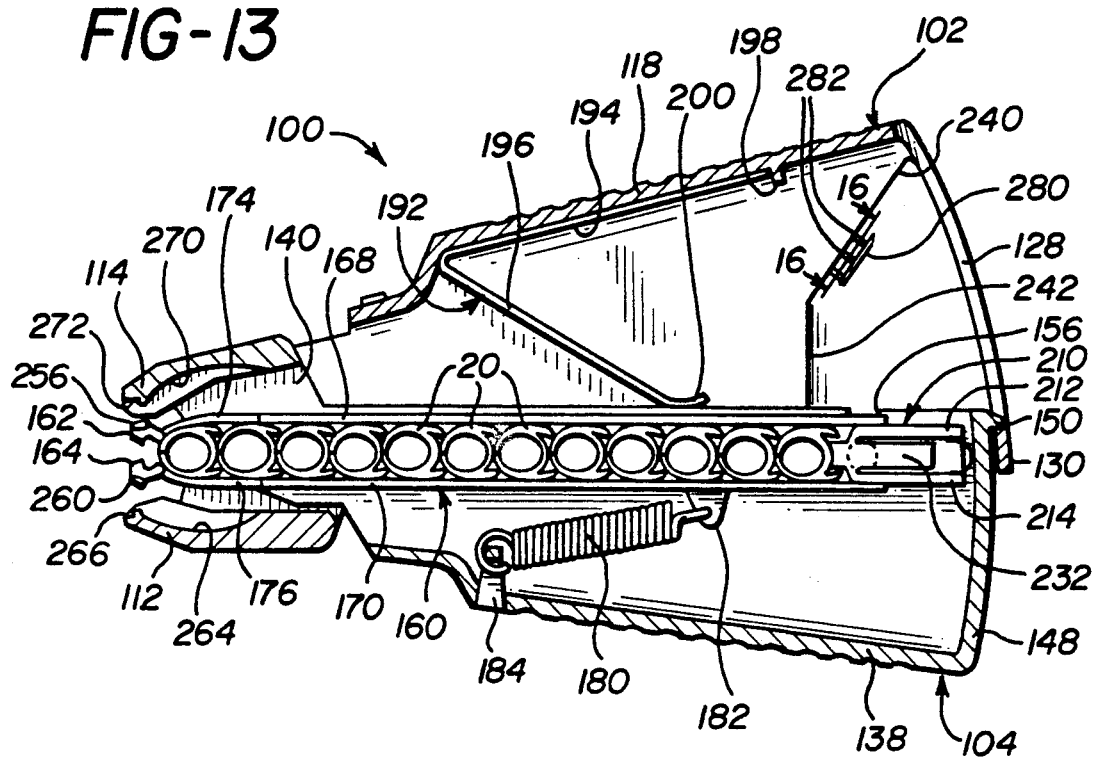
FIG. 13 is a partially cutaway side view of the surgical clip applier.

As shown in FIG. 11, the scalp clip applier 100 includes a housing which is provided by two hollow housing sections, i.e., an outer housing section 102 and an inner housing section 104 which are mounted together for pivotal movement about a pivot axis 106 located toward the front of the housing sections. The outside dimensions (length and width) of inner housing section 104 are less than the inside dimensions (length and width) of upper housing section 102 so that the inner housing section 104 is received within the outer housing section 102 when the housing sections are pivoted together As shown in FIGS. 11 and 13, the outer housing section 102 and the inner housing section 104 are flared rearwardly and provided with a series of serrations or finger grips 108 and 110, respectively, to facilitate the handling and operation of the surgical clip applier 100 by a surgeon. The front portions of outer housing section 102 and inner housing section 104 extend forwardly beyond the pivot axis 106 to form clip actuating jaws 112 and 114, respectively.

Referring to the assembly view of FIG. 19, outer housing section 102 includes a pair of flat parallel side walls 116 connected by a convex top wall 118 on which the serrations 108 are formed. The front portion of outer housing section 102 includes a pair of spaced, vertical flanges 120 which extend downwardly from the side walls 116 and are connected at the bottom to the lower clip actuating jaw 112. The top convex wall 118 of outer housing section 102 terminates at a point adjacent to flanges 120 to provide an opening 124 at the front of the outer housing section 102 for receiving the upper clip actuating jaw 114 at the front portion of the inner housing section 104. On the inner surfaces of vertical flanges 120, a pair of circular recesses 126 (one shown) is formed which define the pivot axis 106 of the housing. An assembly slot 134 extends horizontally from the rear of each flange 120 to the circular recess 126. Each slot 134 has an outwardly flared or chamfered rear edge 135 to facilitate assembly.

Similarly, as shown in FIGS. 13 and 18, the inner housing section 104 includes a pair of flat parallel side walls 136 connected by a convex bottom wall 138 on which the serrations 110 are formed. The front portion of inner housing section 104 includes a pair of spaced, vertical flanges 140 which extend upwardly from the side walls 136 and are connected at the top to the upper clip actuating jaw 114. The bottom convex wall 138 of inner housing section 104 terminates at a point adjacent to flanges 140 to provide an opening 142 (FIG. 15) at the front of the inner housing section 104. Referring to FIG. 19, on the outer surfaces of vertical flanges 140, a pair of cylindrical projections 144 (one shown) is formed which are received within the circular recesses on flanges 120 to connect the outer housing section 102 and the inner housing section 104 together for pivotal movement about the pivot axis 106. Each cylindrical projection 144 has an inwardly flared or chamfered front edge 146 to facilitate assembly.

As shown in FIG. 13, the back of outer housing section 102 includes a curved rear wall 128 terminating at a downwardly projecting flange 130. A vertical slit 132 (FIG. 12) is formed in rear wall 128 and extends downwardly from top wall 118 to a point above the bottom of flange 130. The back of inner housing section 104 terminates at a curved rear wall 148. A rearwardly projecting tongue 150 at the top of rear wall 148 is slidably received in vertical slot 132 at the rear of the outer housing section 102.

When the outer housing section 102 and the inner housing section 104 are assembled, the cylindrical projections 146 on flanges 140 are slid into the slots 134 and snap fit into the circular recesses 126 on flanges 120 to pivotally connect the outer housing section 102 and the inner housing section 104 together. Also, the rearwardly projecting tongue 150 is snap fit into the vertical slot 132 to hold the outer housing section 102 and inner housing section 104 together. The tongue 150 serves as a stop to limit the extent of outward pivotal movement of the housing sections 102 and 104.

As shown in FIG. 19, a series of equally spaced rectangular windows or slots 152 are formed in one side wall 136 of inner housing section 104. The slots 152 are uniformly spaced apart and arranged in a straight line at a distance slightly below the top of side wall 136. An elongated horizontal slot 154 is formed in the opposite side wall 136 at the rear of inner housing section 104. The front end of horizontal slot 154 opens into a vertical slot 156 which extends to the top of the side wall 136 of the inner housing section 104. The purposes of vertical slots 152 and horizontal slot 154 are explained below.

Referring to FIGS. 13 and 19, the surgical clip applier 100 includes an elongated clip sleeve 160 which is adapted to receive a plurality of surgical clips 20 arranged front to back in a row. An open front end of the clip sleeve 160 extends forwardly between the upstanding vertical flanges 140 on the inner housing section 104. The clip sleeve 160 includes a pair of clip retaining jaws 162 and 164 adjacent to an open front end of the clip sleeve 160.

As shown in FIG. 19, the clip sleeve 160 is channel-shaped in configuration and includes an elongated rectangular side wall 166 from which project an elongated rectangular top flange 168 and an elongated rectangular bottom flange 170. At the front of clip sleeve 160, an elongated rectangular tongue 172 projects forwardly from the top flange 168. The tongue 172 is flanked by a pair of fingers 174 which also project forwardly from the top flange 168. The upper clip retaining jaw 162 extends transversely across the front end of tongue 172. Similarly, an elongated, rectangular tongue 176 projects forwardly from the bottom flange 120. The tongue 176 is flanked by a pair of elongated fingers 178. The lower clip retaining jaw 164 extends transversely across the front end of tongue 176. The tongues 172 and 176 and the fingers 174 and 178 are flexible so that the frontmost surgical clip in the clip sleeve 160 can be advanced outward from the open front end of the sleeve and captured between clip retaining jaws 162 and 164. When the frontmost surgical clip is held between the clip retaining jaws 162 and 164, the fingers 174 and 178 engage the next clip in the row so that the remaining clips are retained in the clip sleeve 110 and out of engagement with the frontmost clip. Also, the fingers 174 and 178 prevent a clip loaded between jaws 162 and 164 from moving backward into the clip sleeve 160.

Figure 23:
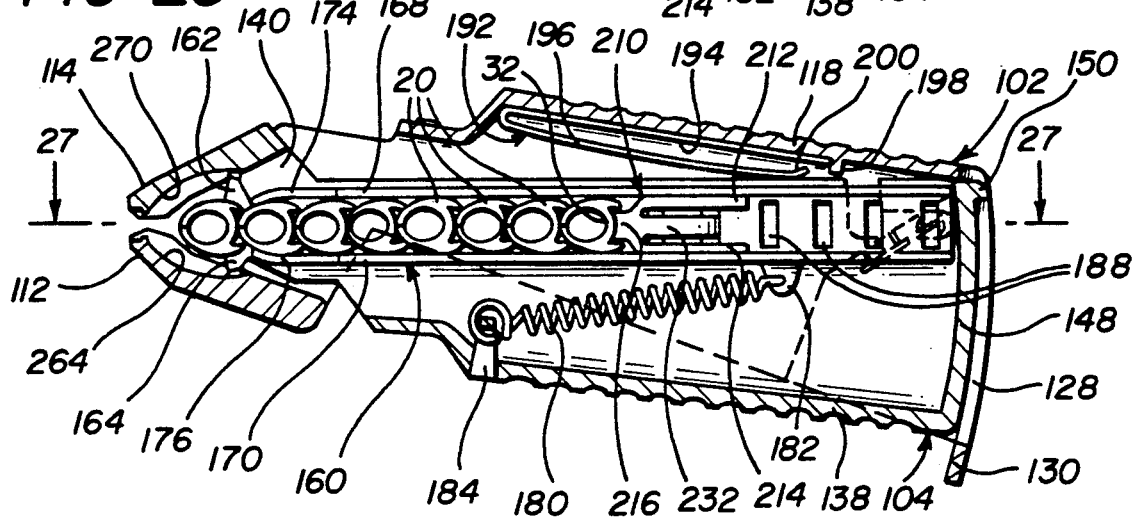

Clip sleeve 160 is mounted for longitudinal reciprocating movement relative to the applier housing between a forward position (FIGS. 13 and 20) and a retracted position (FIG. 23). When the clip sleeve 160 is located in its forward position (FIG. 20), the clip retaining jaws 162 and 164 are positioned between the clip actuating jaws 112 and 114.

Figure 14:
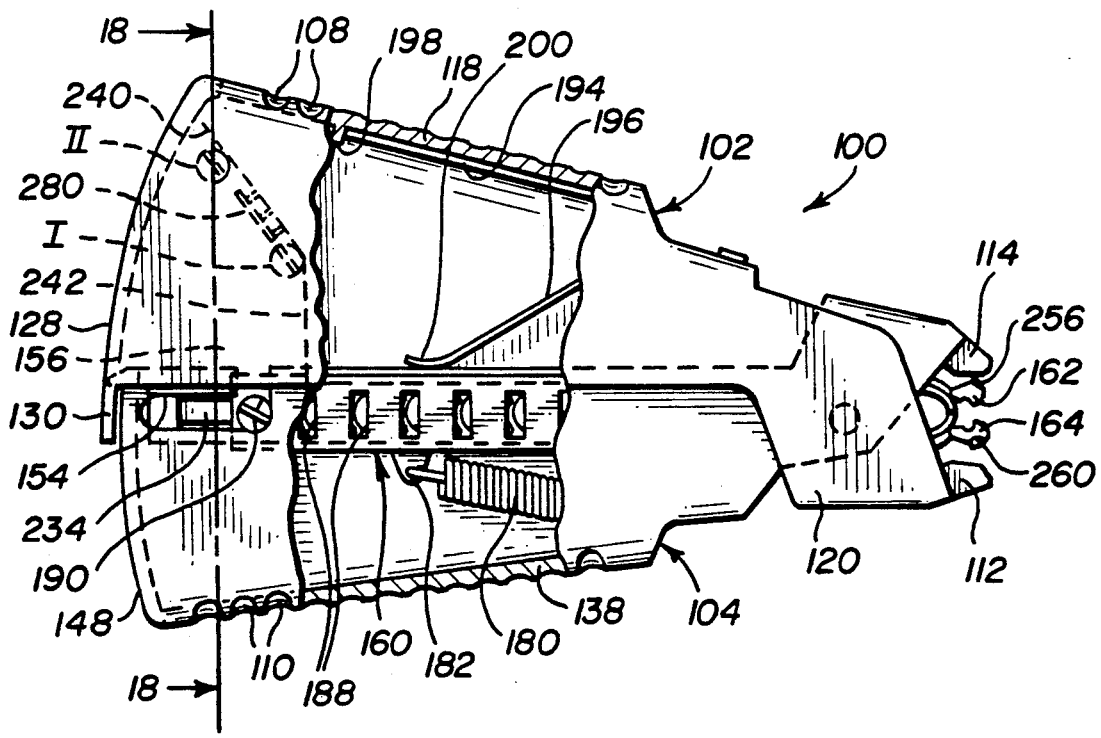
FIG. 14 is a partially cutaway side view showing the opposite side of the surgical clip applier.

A coil spring 180 is connected between a depending lug 182 on the bottom of flange 170 and a fitting 184 inside the inner housing section 104 to normally urge the clip sleeve 160 toward its forward position (FIG. 13). The clip sleeve 160 includes an laterally projecting cylindrical boss 190 (FIG. 14) located at the rear of the side wall 166 which is slidably received within the horizontal slot 154 at the rear of the inner housing section 104. Under the action of coil spring 180, the clip sleeve 160 is urged forwardly and the cylindrical boss 190 engages the front end of the horizontal slot 154 to maintain the clip sleeve 160 in its forward position.

A leaf spring 192 is located inside the outer housing section 102 and normally urges the housing sections 102 and 104 apart. The leaf spring 192 comprises an elongated metal strip which is bent at an acute angle to define an upper spring arm 194 and a lower spring arm 196. The upper spring arm 194 engages a flange 198 (FIG. 24) depending from the top wall 118 of the outer housing section 102. The lower spring arm 196 has a curved end 200 which engages the top of the inner housing section 104.

As shown in FIG. 19, side wall 166 of the clip sleeve 160 includes an extension 186 at the front of the clip sleeve 160. The extension 186 serves as a guide for the surgical clips 20 which are advanced outward from the open front end of the clip sleeve 160. A plurality of uniformly spaced vertical slots or windows 188 are formed in the side wall 166 of the clip sleeve 160. The rearmost slot 188 (FIG. 26) on the clip sleeve 160 is formed as a recessed notch, rather than a window, in the side wall 166 opposite to the cylindrical boss 190. The purpose of the vertical slots 188 is explained below.

A pusher 210 is slidably mounted on the clip sleeve 160 for engaging the rearmost surgical clip in the row. The pusher 210 is movable one step at a time along the clip sleeve 160 to advance the row of clips toward the open front end of the clip sleeve 160. The length of each step is determined by the spacing between the vertical slots 152 and 188 provided in the inner housing section 104 and the clip sleeve 160. The slots 152 and 188 are uniformly spaced apart by a distance equal to the stack length "L" occupied by one surgical clip 20 in the row. As shown in FIG. 9, the stack length "L" is equal to the horizontal distance between the front of the shoulders 50 and 62 and the rear of the ledges 70 and 76 on flanges 38 and 40 of one surgical clip 20.

As shown FIGS. 13 and 19, the pusher 210 is generally an elongated C-shaped body including an upper flange 212 and a lower flange 214 which are slidably received between top flange 168 and bottom flange 170 of the clip sleeve 160. A nose 216 extends transversely across the front of the pusher 210 and includes a concave clip engaging surface 218. As shown in FIG. 32, at the point where the nose 216 meets the front of the pusher body, a steeply sloped upper face 220 extends upwardly from the top of nose 216 to the upper flange 212. Similarly, a steeply sloped lower face 222 extends downwardly from the bottom of nose 216 to the lower flange 214. As shown in FIG. 19, a central portion of the upper front face 220 is indented to provide a flat inclined surface 224 which slopes gradually upward to the upper flange 212 of the pusher body. Similarly, a central portion of the lower front face 222 is indented to form a flat inclined surface 226 which slopes gradually downward to the lower flange 224 of the pusher body.

Preferably, the upper front face 220 and the lower front face 222 are sloped at an angle of 15 degrees from the vertical. Also, the upper inclined surface 224 is sloped upwardly at an angle of 15 degrees to the horizontal, and the lower inclined surface 226 is sloped downwardly at an angle of 15 degrees to the horizontal.

Figure 26:
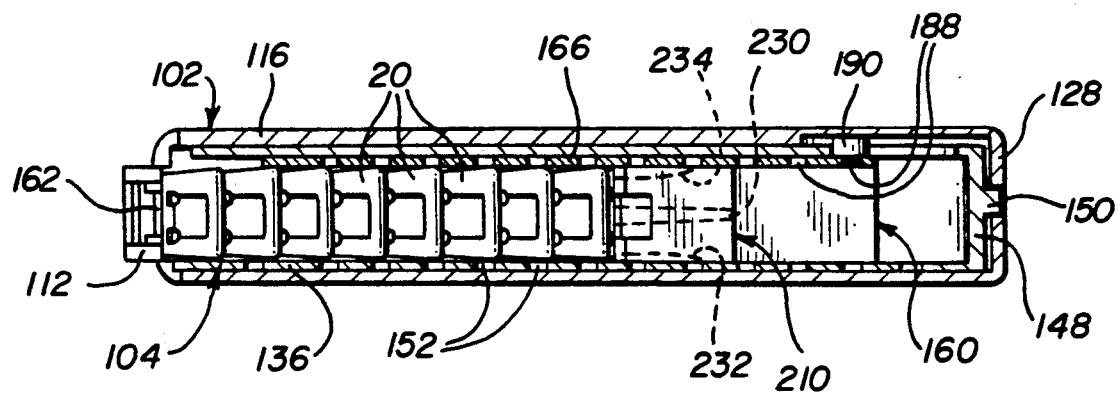
FIG. 26 is a horizontal section of the surgical clip applier taken along line 26—26 of FIG. 20.

As shown in FIG. 33, the nose 216 of the pusher 210 has its opposite edges 228 tapered inwardly, preferably at an angle of 10 degrees, to the centerline of the pusher body. An elongated vertical reinforcing web 230 is located inside the pusher body. The web 230 extends rearwardly from the nose 216 and connects flanges 212 and 214 together. The pusher 210 includes a pair of flexible arms 232 and 234 which extend rearwardly along opposite sides of the pusher body. As shown in FIG. 26, a rear portion of arm 232 is curved outwardly from the pusher body and is received by the windows 152 formed in the inner housing section 104. Similarly, a rear portion of arm 234 is curved outwardly from the pusher body and is received by the windows 188 formed in the side wall 166 of the clip sleeve 160. The windows 152 and pusher arm 232 provide a first ratchet mechanism for controlling the movement of the pusher 210 relative to the inner housing section 104. The windows 188 and pusher arm 234 provide a second ratchet mechanism for controlling the movement of the pusher 210 relative to the clip sleeve 160. As explained below, these ratchet mechanisms are operable each time the clip sleeve 160 is reciprocated for advancing the pusher 210 and the row of clips by one step along the clip sleeve 160.

In the preferred embodiment of the surgical clip applier, a cam mechanism is provided for reciprocating the clip sleeve 160 relative to the applier housing. Referring to FIGS. 13 and 18, the cam mechanism comprises an inclined cam surface or ledge 240 formed by an offset or cutaway portion on the inside of one side wall 116 at the rear of the outer housing section 102. The inclined cam surface 240 slopes downwardly and forwardly from the rear wall 128 of the outer housing section 102 to an intermediate point thereon where the cam surface 240 joins a straight, rearwardly facing surface or ledge 242 which extends vertically downward to the bottom of the outer housing section 102. The inclined cam surface 240 engages the cylindrical boss 190 (FIG. 14) to reciprocate the clip sleeve 160 longitudinally when the housing sections 102 and 104 are pivoted together.

Referring to FIGS. 19 and 29, each of the clip retaining jaws 162 and 164 comprises an enlarged head formed as extension of the tongues 172 and 176 at the open front end of the clip sleeve 160. A pair of clip receiving grooves 252 and 254 extends transversely across the opposed faces of jaws 162 and 164. The upper clip retaining jaw 162 includes an upwardly projecting ridge 256 which extends transversely across the top of the clip retaining jaw 162. As shown in FIG. 19, the ridge 256 extends laterally outward from the opposite sides of the upper clip retaining jaw 162. The ridge 256 has a sloped rear edge 258 (FIG. 29) which is normally sloped at an angle of 20 degrees to the vertical. The lower clip retaining jaw 164 includes a downwardly projecting ridge 260 extending transversely across the bottom of the clip retaining jaw 164. As shown in FIG. 19, the ridge 260 extends laterally outward from the opposite sides of the lower clip retaining jaw 164. The ridge 260 has a sloped rear edge 262 (FIG. 29) which is normally sloped at an angle of 20 degrees to the vertical. The width of the clip retaining jaws 162 and 164 (FIG. 17) is selected to allow the jaws 162 and 164 to be received in the indentations 42 and 54 (FIG. 3) between the ramp-like surfaces 46 and 58 of the clip body.

As shown in FIGS. 19 and 29, the inside of the lower clip actuating jaw 112 is cut away to provide a concave groove 264 extending rearwardly from the front end of the jaw 112. A flat ledge 266 is located at the front of groove 264 for engaging the lower clip retaining jaw 164. The ledge 266 terminates at a raised lip 268 for engaging the rear edge 262 of the ridge 260 on the lower clip retaining jaw 164. The groove 264 is sufficiently wide to receive the lower clip retaining jaw 162 when the clip actuating jaws are pivoted toward each other. Also, the inside of the upper clip actuating jaw 114 is cut away to provide a concave groove 270 extending rearwardly from the front end of the jaw 114. A flat ledge 272 is located at the front end of groove 270 for engaging the upper clip retaining jaw 162. The ledge 272 terminates at a raised lip 274 for engaging the rear edge 258 of the ridge 256 on the upper clip retaining jaw 162. The groove 270 is sufficiently wide to receive the upper clip retaining jaw 164 when the clip actuating jaws are pivoted toward each other.

Referring to FIG. 13, an elongated guide rail 280 extending parallel to the cam surface 240 is provided on the side wall 116 of the outer housing section 102. A plurality of evenly spaced ratchet teeth 282 are formed on the side wall 116 between cam surface 240 and guide rail 280. When the outer housing section 102 and the inner housing section 104 are pivoted together, cam surface 240 engages the cylindrical boss 190 on the clip sleeve 160. As shown in FIG. 32, the cylindrical boss 190 includes a slot 284 oriented at an angle to receive guide rail 280 as the cam surface is moved along the cylindrical boss 190. Above the slot 284, a portion of the cylindrical boss 190 is cut away to define a lip 286 at the outer end of the cylindrical boss 190 oriented perpendicularly to the slot 284. The lip 286 on the cylindrical boss 190 acts as a pawl for engaging the ratchet teeth 282 (FIG. 16). As the cylindrical boss 190 is moved by the cam surface 240 along the guide rail 280, the lip 286 on the cylindrical boss 190 engages the ratchet teeth 282 which prevent the cylindrical boss 190 from returning along the guide rail 280. The lip 286 and the ratchet teeth 282 act as a latch mechanism which prevents the housing sections 102 and 104 from pivoting apart until the cylindrical boss 190 is advanced beyond the guide rail 280.

As shown in FIG. 13, with the clip applier 100 fully loaded, there are twelve clips arranged front to back within the clip sleeve 160. The pusher 210 is located at the rear of the clip sleeve 160 with its flanges 212 and 214 protruding rearwardly from the clip sleeve 160 and its nose 216 engaging the rearmost clip 20 in the row. The frontmost clip 20 is engaged by the tongues 172 and 176 and the fingers 174 and 178 at the front of the clip sleeve 160 to retain the row of clips 20 within the clip sleeve 160. Coil spring 180 urges the clip sleeve 160 forwardly and the cylindrical boss 190 (FIG. 14) on the clip sleeve 160 engages the front edge of slot 154. As a result, the clip sleeve 160 is located in its forward position with the clip retaining jaws 162 and 164 located between the clip actuating jaws 112 and 114. The leaf spring 192 located inside the outer housing section 102 engages the top of the inner housing section 104 and normally biases the housing sections 102 and 104 apart.

In operation, the surgical clip applier 100 is gripped in the hand of a surgeon and the housing sections 102 and 104 are manually pivoted together to advance the surgical clips 20 one at a time from the clip sleeve 160 and to actuate the clip actuating jaws 112 and 114. The surgical clip applier 100 is operated with a double pump action illustrated in FIGS. 20-25 in which the housing sections 102 and 104 are twice pivoted together and released. For purposes of illustration, the pusher 210 is shown without its vertical web 230. In the first pump action, the housing sections 102 and 104 are pivoted together and released for a first time to advance the surgical clips 20 along the clip sleeve 160 one at a time to the clip retaining jaws 162 and 164. In the second pump action, the housing sections 102 and 104 are pivoted together and released for a second time to operate the clip actuating jaws 112 and 114 to actuate the surgical clip held by the clip retaining jaws 162 and 164.

During the first pump action (FIGS. 21-23) of the surgical clip applier 100, when the housing sections 102 and 104 are manually pivoted together for the first time, the clip sleeve 160 is retracted into the applier housing. As the clip sleeve is retracted, the frontmost surgical clip is advanced outward from the open front end of the clip sleeve 160 and loaded between the clip retaining jaws 162 and 164. When the clip sleeve 160 returns to its original position (FIG. 24), the surgical clip 20 held by the clip retaining jaws 162 and 164 is advanced to a load position between the clip actuating jaws 112 and 114.

During the second pump action (FIG. 25) of the surgical clip applier 100, when the housing sections 102 and 104 are pivoted together for a second time, the clip actuating jaws 112 and 114 engage the clip retaining jaws 162 and 164 to open the surgical clip 20 to receive a tissue flap. Then, the housing sections 102 and 104 are released and pivot outwardly to allow the surgical clip 20 to close about the tissue flap. The surgical clip 20 is released from the clip retaining jaws 162 and 164 by drawing the surgical clip applier 100 away from the tissue. As a result, the surgical clip 20 remains clamped to the tissue flap for hemostatic purposes.

Figure 20:
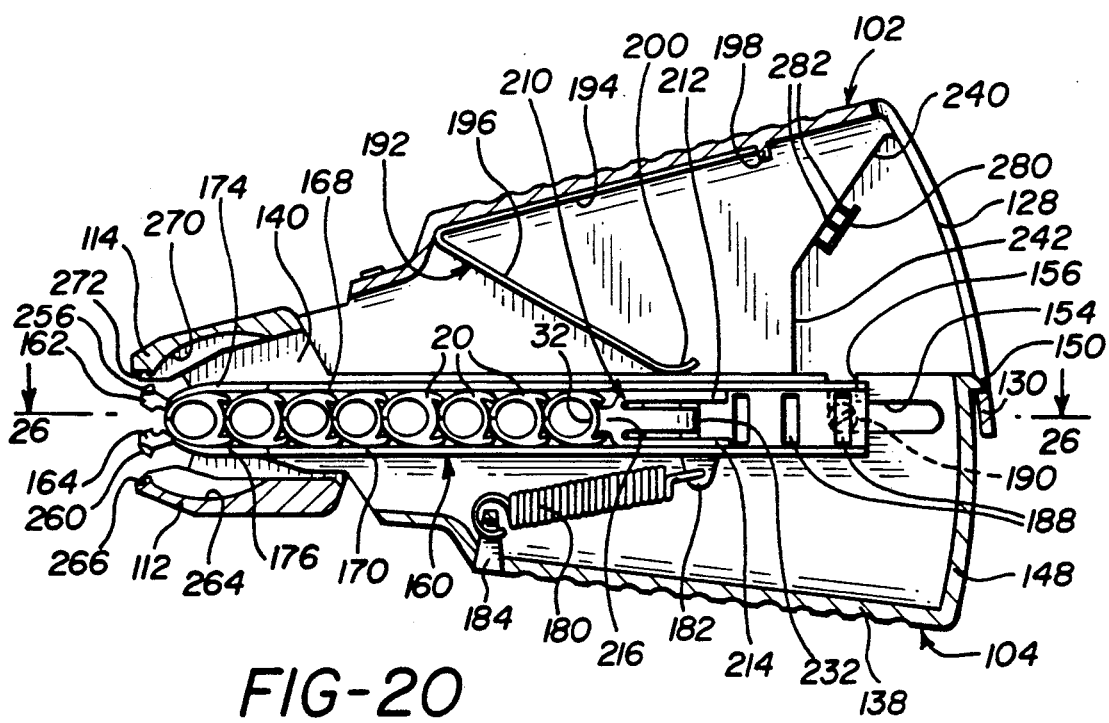
FIG. 20 is a partially cutaway side view of the surgical clip applier with the clip sleeve in the forward position.

Referring to FIG. 20, for purposes of illustration, the surgical clip applier 100 is shown after it has been operated four times to advance four surgical clips 20 from the clip sleeve 160 and to apply the surgical clips 20 to a tissue flap (not shown). Thus, after four operations of the surgical clip applier, eight surgical clips 20 remain within the clip sleeve 160. The clip sleeve 160 is urged by the coil spring 180 to the forward position with the cylindrical boss 190 engaged with the front end of the horizontal slot 154. The nose 216 of the pusher 210 engages the bridge 36 of the rearmost surgical clip 20. The surgical clips 20 are arranged front to back in a row. The frontmost surgical clip 20 is retained within the clip sleeve 160 by the front fingers 174 and 176 which engage the ramp-like surfaces 46 and 58 (FIGS. 1 and 2), respectively, on the frontmost surgical clip 20. As shown in FIGS. 9 and 10, the surgical clips 20 are maintained in alignment and relative rotation is precluded by the front notches 52 and 54 of each surgical clip 20 which receive the rear tabs 70 and 74 of the next surgical clip 20 in the row. Also, the surgical clips 20 are maintained in alignment and relative rotation is precluded by the front shoulders 50 and 62 on each surgical clip 20 which engage the rear ledges 72 and 76, respectively, on the flanges 38 and 40 of the next surgical clip 20 in the row. As shown in FIG. 26, the free end of arm 232 on pusher 210 is received within one of the vertical slots or windows 152 formed in the inner housing section 104. Similarly, the free end of arm 234 on the pusher 210 is received within one of the vertical slots or windows 188 formed in the side wall 166 of the clip sleeve 160.

Figure 21:
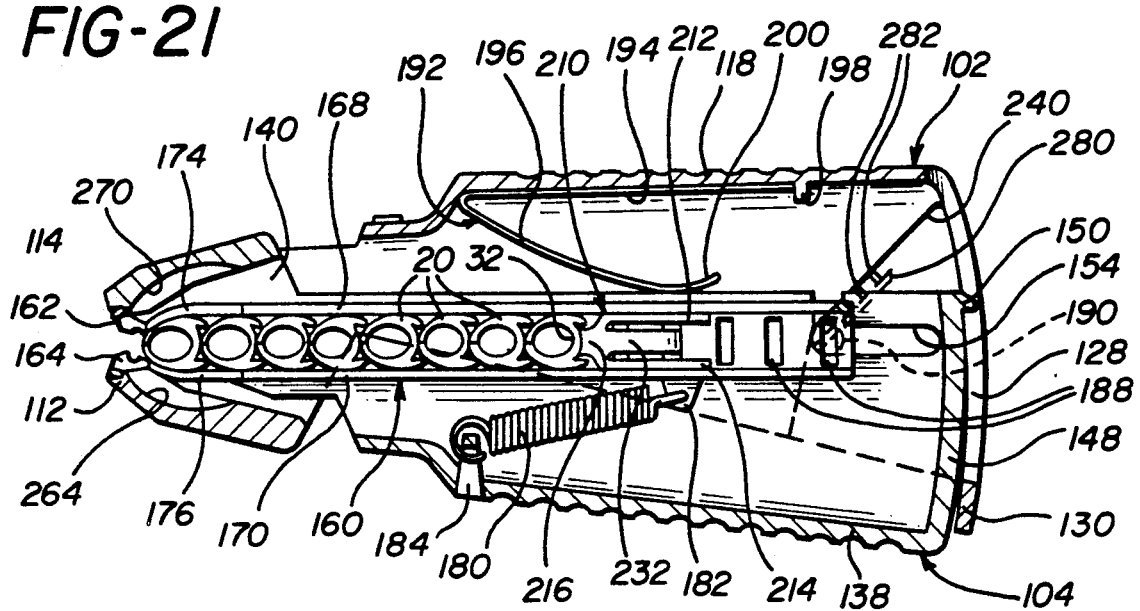
FIGS. 21-23 are partially cutaway side views illustrating the operation of the surgical clip applier to move the clip sleeve to the retracted position.

Initially, when the housing sections 102 and 104 are pivoted together for the first time (FIG. 21), the cam surface 240 is moved downward into a first position where the cylindrical boss 190 is engaged by the front portion of the cam surface 240. At this point, the position of cylindrical boss 190 relative to the cam surface 240 is indicated by phantom lines I in FIG. 14. As shown in FIG. 21, with the housing sections 102 and 104 pivoted together, the clip actuating jaws 112 and 114 are moved into engagement with the clip retaining jaws 162 and 164. With the cylindrical boss 190 at position I, the clip sleeve 160 remains in its forward position with the cylindrical boss 190 engaged with the front end of the slot 154.

Figure 22:
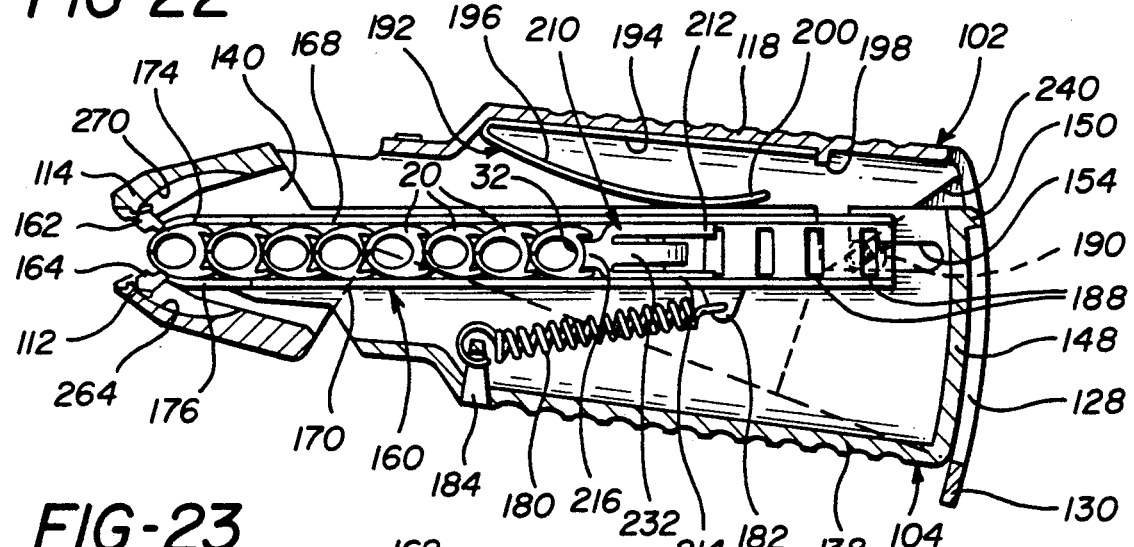

Next, as shown in FIG. 22, when the housing sections 102 and 104 are pivoted closer together, the cam surface 240 is moved downward to a second position where the cylindrical boss 190 is moved along the guide rail 280. The clip sleeve 160 is retracted into the housing against the bias of coil spring 180 under the action of inclined cam surface 240 which engages and slides the cylindrical boss 190 backward along slot 154. The pusher 210 remains stationary relative to the inner housing section 104 because the free end of the pusher arm 232 engages the rear edge of one of the vertical slots 152. At the same time, the side wall 166 of clip sleeve 160 bends arm 284 inwardly to allow the clip sleeve 160 to be retracted relative to the pusher 210. Since the pusher 210 remains stationary, the row of surgical clips 20 also remains stationary while the clip sleeve 160 is retracted.

As the clip sleeve 160 is retracted, the clip retaining jaws 162 and 164 are initially deflected toward each other when the ridges 256 and 260 slide over the raised lips 264 and 274 (FIG. 29) on the clip actuating jaws 112 and 114. Subsequently, the clip retaining jaws 162 and 164 are spread apart as the tongues 172 and 176 (FIG. 19) move across the frontmost surgical clip 20 in the clip sleeve 160. The clip retaining fingers 174 and 176 are spread apart by the ramp-like surfaces 46 and 58 (FIGS. 1 and 2) at the edges of the frontmost surgical clip 20. The clip retaining jaws 162 and 164 are received by the indentations 42 and 54 (FIGS. 1 and 2) in the surgical clip body and are guided along the flat, recessed surfaces 44 and 56 between the ramp-like surfaces 46 and 58, respectively, toward the ridges 48 and 60 at the rear of the flanges 38 and 40, respectively.

As the cam surface 240 is moved along the cylindrical boss 190, the guide rail 280 which extends parallel to the cam surface 240 is slidably received in the slot 284 formed in the face of the cylindrical boss 190. The lip 286 on the end of the cylindrical boss 190 engages the ratchet teeth 282 located between the cam surface 240 and the guide rail 280 to prevent the housing sections 102 and 104 from pivoting apart until the cylindrical boss 190 is advanced beyond the guide rail 280.

Figure 27:
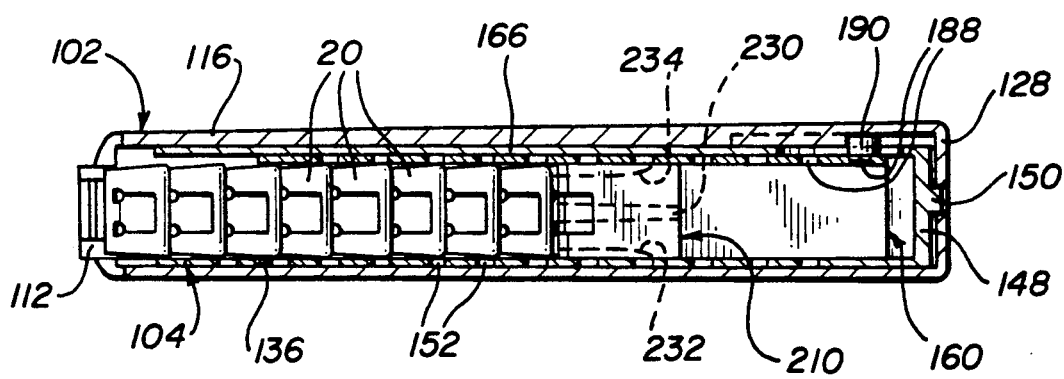
FIG. 27 is a horizontal section of the surgical clip applier taken along line 27—27 of FIG. 23.

As shown in FIG. 23, when the housing sections 102 and 104 are further pivoted together, the cam surface 240 is moved downward to a third position where the cylindrical boss 190 is moved beyond the guide rail 280 and the clip sleeve 160 is moved to its retracted position. At this point, the position of the cylindrical boss 190 relative to the cam surface 240 is indicated by the phantom lines 11 shown in FIG. 14. As shown in FIG. 23, with the clip sleeve 160 fully retracted into the housing the clip retaining jaws 162 and 164 are moved into engagement with the rear flanges 38 and 40 on the frontmost surgical clip 20. Since the row of surgical clips 20 is held stationary by the pusher 210, the frontmost surgical clip 20 is advanced outward from the open front end of the clip sleeve 160. The ridges 48 and 62 (FIG. 7) on the rear flanges 38 and 40 of the surgical clip 20 are captured by the grooves 262 and 264 (FIG. 29) in the clip retaining jaws 162 and 164. As shown in FIG. 27, the arm 234 on the pusher 210 engages the next vertical slot or window 188 in the side wall 166 so that, in effect, the pusher 210 and the row of clips are advanced by one step relative to the clip sleeve 160.

Figure 24:
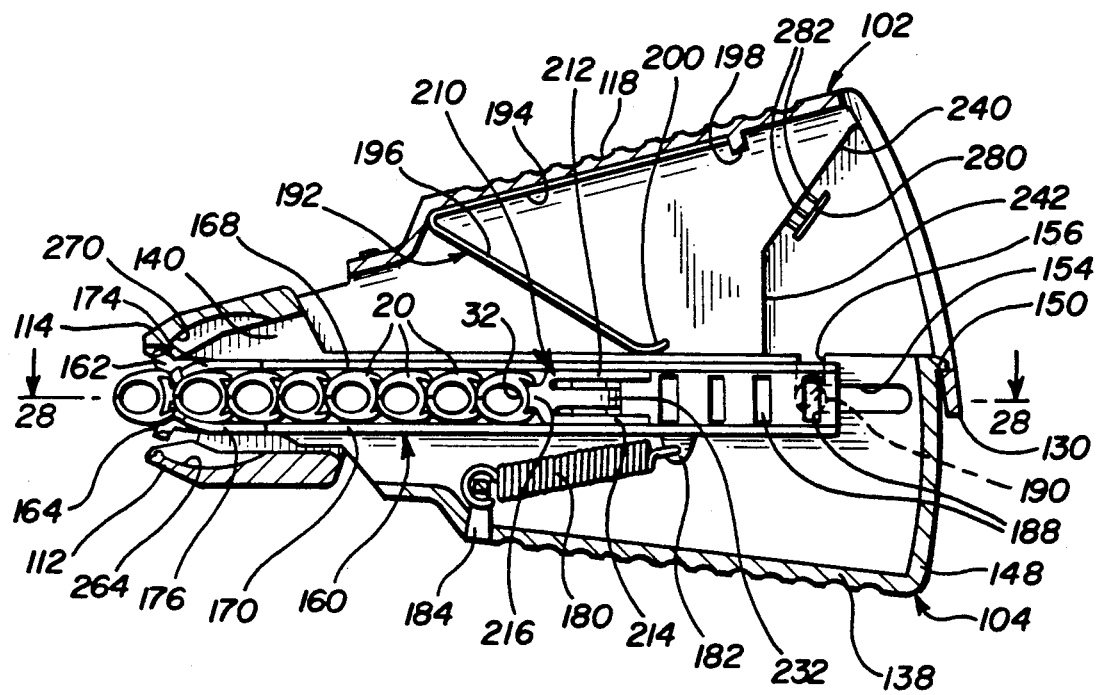
FIG. 24 is a partially cutaway side view of the surgical clip applier with the clip sleeve returned to the forward position.

Next, as shown in FIG. 24, the housing sections 102 and 104 are released and pivot under the action of the leaf spring 192 to the fully open position. As a result, the clip sleeve 160 is advanced by the coil spring 180 to its forward position with the cylindrical boss 190 engaged with the front end of slot 154. With the clip sleeve 160 returned to its original position, the surgical clip 20 held by the clip retaining jaws 162 and 164 is advanced to a load position between the clip actuating jaws 112 and 114. The pusher 210 is held in a fixed position relative to the clip sleeve 160 because the free end of arm 234 engages the rear edge of the vertical slot or window 188 in the side wall 166 of the clip sleeve 160. As the clip sleeve 160 is advanced, the arm 232 on the pusher 210 is bent inwardly by the side wall 136 of the inner housing section 104 to allow the arm 232 to be advanced forwardly to engage the next vertical slot or window 152.

Figure 28:
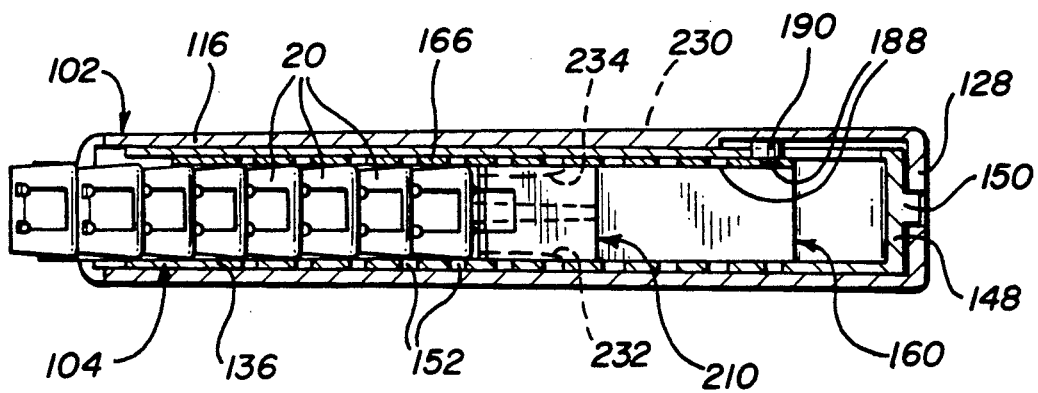
FIG. 28 is a horizontal section of the surgical clip applier taken along line 28—28 of FIG. 24.

Referring to FIGS. 26-28, the arms 232 and 234 on opposite sides of the pusher 210 and the corresponding vertical slots or windows 152 and 188 provided in the inner housing section 104 and the clip sleeve 160, respectively, provide a dual ratchet mechanism for advancing the pusher 210 and the row of clips one step at a time along the clip sleeve 160. As shown in FIG. 26, before the clip sleeve 160 is reciprocated, the arm 232 on the pusher 210 extends into one of the vertical slots or windows 152 formed in the inner housing section 104 and the arm 234 on the pusher 210 projects into an opposed vertical slot or window 188 formed in the side wall 166 of the clip sleeve 160.

When the clip sleeve is retracted (FIG. 27), the free end of the arm 232 on pusher 210 engages the rear edge of the slot 152 to hold the pusher 210 and the row of surgical clips 20 stationary relative to the inner housing section 104. As a result, the clip sleeve 160 is moved backward relative to the pusher 210 and the row of surgical clips 20 to capture the frontmost clip 20 between the clip retaining jaws 162 and 164. As the clip sleeve 160 is retracted, the arm 234 on the opposite side of the pusher 210 is bent inwardly by the side wall 166 of the clip sleeve 160 so that, in effect, the arm 234 is advanced to the next slot 188 of the clip sleeve 160.

When the clip sleeve 160 is advanced to its forward position (FIG. 28), the arm 234 on the pusher 210 engages the rear edge of the slot 188 so that the pusher 210 and the row of surgical clips 20 are moved forward with the clip sleeve 160. As the clip sleeve 160 is advanced, the arm 232 on the pusher 210 is bent inwardly as it travels across the inside of the inner housing section 104 to the next slot 152. After the frontmost surgical clip 20 is released from the clip retaining jaws 162 and 164, the dual ratchet mechanism can be actuated again to advance the next surgical clip 20 from the clip sleeve 160 to the clip retaining jaws 162 and 164.

During the second pump stage (FIG. 25) of the surgical clip applier 100, when the housing sections 102 and 104 are manually pivoted together for a second time, the clip actuating jaws 112 and 114 pivot into contact with the clip retaining jaws 162 and 164. As the clip actuating jaws 112 and 114 are pivoted together, the front ledges 266 and 272 (FIG. 30) engage the ridges 256 and 260 of the clip retaining jaws 162 and 164 to apply pressure to the rear flanges 38 and 40 of the surgical clip 20 to open the front end of the surgical clip 20 to receive a tissue flap therein. The rear edges 258 and 262 of the ridges 256 and 260 on the clip retaining jaws 162 and 164 are engaged by the raised lips 268 and 274 inside the clip actuating jaws 112 and 114, respectively, to maintain the clip sleeve 160 in its forward position and to prevent the clip retaining jaws 162 and 164 from retracting into the housing. As the housing sections 102 and 104 are pivoted together to apply more pressure via the clip actuating jaws 112 and 114 to the clip retaining jaws 162 and 164, the surgical clip 20 is fully opened (FIG. 30). When the surgical clip 20 is fully opened, the tabs 70 and 74 on the rear flanges of the clip body act as stop members which engage each other to limit the maximum opening of the surgical clip 20. As a result, the ridges 256 and 260 on clip retaining jaws 162 and 164 are maintained in engagement with the raised lips 268 and 270 on the clip actuating jaws 112 and 114.

Figure 25:
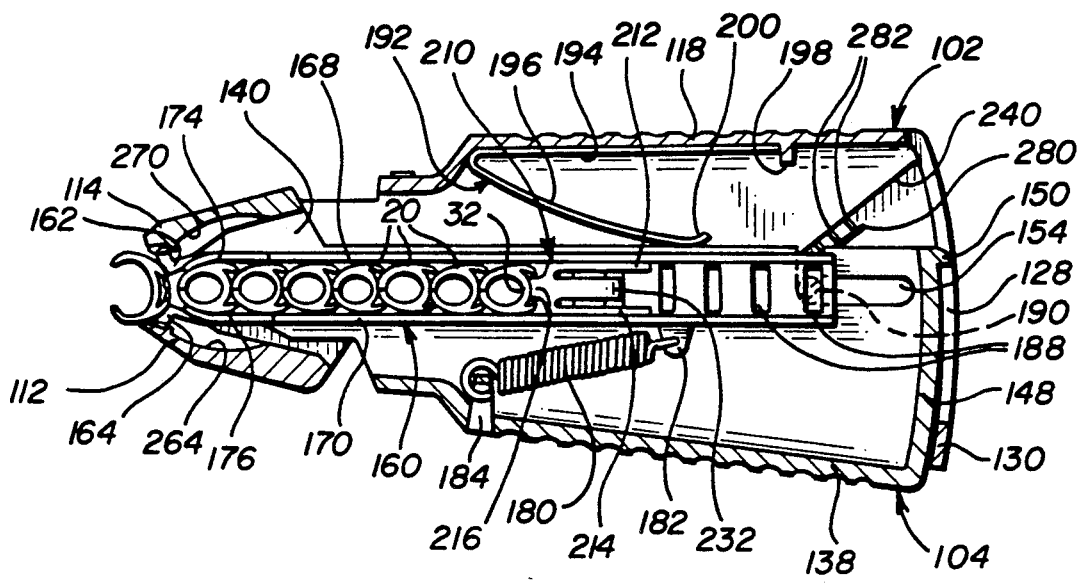
FIG. 25 is a partially cutaway side view illustrating the actuation of a surgical clip by the surgical clip applier.

As shown in FIG. 25, when the surgical clip 20 is fully open and its tabs engaged, the inward pivotal movement of the housing sections 102 and 104 is stopped with the cylindrical boss 190 out of engagement with the inclined cam surface 240. The cylindrical boss 190 remains at the front of the slot 154 and the clip sleeve 160 remains in its forward position while the clip 20 is open.

After the tissue flap is positioned within the open surgical clip, the housing sections 102 and 104 are released and pivoted outwardly by the action of the leaf spring 192. As the housing sections 102 and 104 pivot outwardly, the clip actuating jaws 112 and 114 pivot apart to release the pressure applied to the clip retaining jaws 162 and 164. As a result, the surgical clip 20 closes and clamps the tissue flap. The surgical clip 20 is released from the clip retaining jaws 162 and 164 by drawing the surgical clip applier 100 away from the tissue flap.

The above operation of the surgical clip applier 100 can be repeated to apply additional surgical clips 20 to the tissue flap. When it is desired to remove the surgical clip 20 from the tissue flap, a conventional tool, such as a forceps removal tool, can be used to apply pressure to the flanges 38 and 40 on the surgical clip body to open the tissue clamping jaws 22 and 24 to release the surgical clip 20 from the tissue flap.

In the assembly of the surgical clip applier 100, twelve surgical clips 20 are arranged front to back in a row within the clip sleeve 160. The pusher 210 is positioned at the rear of the clip sleeve 160 with its nose 216 engaging the bridge 36 of the rearmost surgical clip 20. The coil spring 180 is attached to the depending lug 182 on the clip sleeve 160 and to the fitting 184 inside the inner housing section 104. The front end of the clip sleeve 160 is inserted between the flanges 140 of the inner housing section 104. The cylindrical boss 190 at the rear end of the clip sleeve 160 is inserted through the vertical slot 156 into the horizontal slot 154 on the inner housing section 104. The pusher arm 232 is located in the rearmost slot 152 on the inner housing section 104.

Next, the flanges 140 on the inner housing section 104 and the front end of the clip sleeve 160 are inserted between the flanges 120 on the outer housing section 102. The cylindrical projections 146 on the flanges 140 are slid into the slots 134 and snap fit into the circular recesses 126 on the flanges 120 to pivotally connect the outer housing section 102 and the inner housing section 104 together. The leaf spring 192 is placed inside the outer housing section 102 with its upper spring arm 194 engaged with the depending flange 198 and its lower spring arm 196 on top of the inner housing section 104. Finally, the housing sections 102 and 104 are pivoted together and the rearwardly projecting tongue 150 is snap fit into the vertical slot 132 to hold the housing sections 102 and 104 together.

Referring to FIGS. 15 and 18, the outer housing section 102 includes a tapered or chamfered edge 244 formed at the bottom of the side wall 116 adjacent to the vertical ledge 242. The purpose of the chamfered edge 244 is to facilitate movement of the boss 190 along the inside of the side wall 116 when the housing sections 102 and 104 are pivoted together.

Preferably, the housing sections 102 and 104, the clip sleeve 160, and the pusher 210 are molded from plastic material. The coil spring 180 and the leaf spring 192 are made of steel.

It is contemplated surgical clip applier will be used as a disposable surgical instrument. It is also contemplated that the surgical clips 20 may be resterilized for subsequent use.

The invention in its broader aspects is not limited to the specific details of the preferred embodiments shown and described, and those skilled in the art will recognize that the invention can be practiced with modification within the spirit and scope of the appended claims.

We claim:

1. A surgical clip applier, comprising:
   a housing comprising a pair of housing sections mounted together for pivotal movement about a pivot axis;
   an elongated clip sleeve adapted to receive a plurality of surgical clips arranged front to back in a row, said clip sleeve being mounted for longitudinal reciprocating movement relative to said housing;
   a pair of clip retaining jaws mounted on said clip sleeve and located adjacent to an open front end of said clip sleeve;
   a pusher mounted on said clip sleeve for engaging the rearmost clip in the row, said pusher being movable one step at a time along said clip sleeve to advance the row of clips toward said open front end of said clip sleeve;
   ratchet means operable each time said clip sleeve is reciprocated for advancing said pusher and the row of clips by one-step along said clip sleeve, each step corresponding to the length of one clip in the row; and
   cam means operable when said housing sections are pivoted together for reciprocating said clip sleeve longitudinally to retract and advance said clip sleeve relative to said housing, said clip retaining jaws engaging the frontmost clip in the row as said clip sleeve is retracted and advancing the frontmost clip from said housing as said clip sleeve is advanced.

2. The surgical clip applier of claim 1, which includes:
   a pair of clip actuating jaws on said housing sections for actuating said clip retaining jaws to open and close the surgical clip held by said clip retaining jaws when said housing sections are pivoted relative to each other.

3. The surgical clip applier of claim 1, which includes:
   a set of clip retaining fingers at said front end of said clip sleeve for engaging the next surgical clip in the row when the frontmost clip is advanced and held by said clip retaining jaws to retain the remaining surgical clips within said clip sleeve.

4. The surgical clip applier of claim 3, wherein said ratchet means includes:
   a first ratchet mechanism operable when said clip sleeve is retracted for advancing said pusher and the row of surgical clips by one step relative to said clip sleeve; and
   a second ratchet mechanism operable when said clip sleeve is advanced for advancing said pusher and the row of surgical clips by one step relative to said housing.

5. The surgical clip applier of claim 4, wherein:
   said first ratchet mechanism includes a first pawl formed on said pusher for engaging a plurality of slots formed on said housing; and
   said second ratchet mechanism includes a second pawl formed on said pusher for engaging a plurality of slots formed on said clip sleeve.

6. The surgical clip applier of claim 5, wherein:
   said slots on said housing and said slots on said clip sleeve are uniformly spaced apart by a distance equal to the length occupied by one surgical clip in the row.

7. The surgical clip applier of claim 5, wherein:
   said first and second pawls are located on opposite sides of said pusher.

8. A surgical clip applier for applying a plurality of surgical clips one at a time from a clip sleeve to a tissue flap, comprising:
   a housing comprising first and second housing sections mounted together for pivotal movement about a pivot axis, each housing section having a front portion extending forwardly beyond the pivot axis to form a clip actuating jaw;
   an elongated clip sleeve mounted for longitudinal reciprocating movement relative to said housing between a forward position and a retracted position, said clip sleeve being adapted to receive a plurality of surgical clips arranged front to back in a row;
   each of said surgical clips comprising a tubular body having a pair of tissue clamping jaws defined by an elongated slit extending across the front of said body and a pair of flanges extending rearwardly from opposite sides of said body at positions remote from said slit, said tissue clamping jaws being connected by a flexible bridge at the rear of said body whereby said body may be distended from its original tubular shape by pressure applied to said flanges;
   said clip sleeve including a pair of clip retaining jaws adjacent to an open front end of said clip sleeve and positioned between said clip actuating jaws with said clip sleeve located in said forward position;

a pusher mounted on said clip sleeve for engaging the rearmost clip in the row, said pusher being movable one step at a time along said clip sleeve to advance the row of clips toward said open front end of said clip sleeve;

ratchet means operable each time said clip sleeve is reciprocated for advancing said pusher and the row of clips by one step along said clip sleeve, each step corresponding to the length of one surgical clip in the row; and cam means operable when said housing sections are pivoted together for a first time without a surgical clip between said clip retaining jaws for reciprocating said clip sleeve longitudinally relative to said housing between the forward position and the retracted position, said clip retaining jaws engaging the flanges of the frontmost clip in the row as said clip sleeve is moved to its retracted position and advancing the frontmost clip between said clip actuating jaws as said clip sleeve is moved to its forward position, said clip actuating jaws being movable into engagement with said clip retaining jaws when said housing sections are pivoted together for a second time with a surgical clip between said clip retaining jaws to apply pressure to the flanges and open the surgical clip to receive the tissue flap therein.

9. The surgical clip applier of claim 8, wherein said ratchet means comprises:

a first ratchet mechanism operable when said clip sleeve is retracted for advancing said pusher and the row of surgical clips by one step relative to said clip sleeve; and a second ratchet mechanism operable when said clip sleeve is advanced for advancing said pusher and the row of surgical clips by one step relative to said housing.

10. The surgical clip applier of claim 9, wherein:

said first ratchet mechanism includes a first pawl formed on said pusher for engaging a plurality of slots formed on said housing; and said second ratchet mechanism includes a second pawl formed on said pusher for engaging a plurality of slots formed on said clip sleeve.

11. The surgical clip applier of claim 10, wherein:

said slots on said housing and said slots on said clip sleeve are uniformly spaced apart by a distance equal to the length occupied by one surgical clip in the row.

12. The surgical clip applier of claim 11, wherein:

said first and second pawls are located on opposite sides of said pusher.

13. The surgical clip applier of claim 8, wherein said cam means includes:

a cam follower on said clip sleeve; and a cam surface formed on one of said housing sections and oriented to engage said cam follower when said housing sections are pivoted together to retract said clip sleeve into said housing.

14. The surgical clip applier of claim 13, which includes:

first spring means for normally urging said housing sections to pivot apart; and second spring means for normally urging said clip sleeve toward its forward position.

15. The surgical clip applier of claim 14, which includes:

latch means for retaining said housing sections pivoted together as said cam surface is moved along said cam follower to prevent said housing sections from pivoting apart until said clip sleeve is fully retracted to load the frontmost clip between said clip retaining jaws.

16. The surgical clip applier of claim 15, wherein said latch means comprises:

a guide rail on said one housing section extending parallel to said cam surface;

a slot formed in said cam follower for receiving said guide rail as said cam surface is moved along said cam follower;

a set of ratchet teeth formed on said one housing section between said cam surface and said guide rail; and a lip formed on said cam follower for engaging said ratchet teeth as said cam surface is moved along said cam follower to prevent said cam follower from being disengaged from said guide rail until said clip sleeve is fully retracted.

17. The surgical clip applier of claim 8, which includes:

first stop means on said clip actuating jaws for engaging said clip retaining jaws when said housing sections are pivoted together with a surgical clip held between said clip retaining jaws to maintain said clip sleeve in its forward position and to prevent retraction of said clip sleeve into said housing.

18. The surgical clip applier of claim 17, which includes:

second stop means on said body of said surgical clip for limiting the opening of said surgical clip and maintaining said clip retaining jaws in engagement with said first stop means on said clip actuating jaws.

19. The surgical clip applier of claim 18, wherein:

said second stop means comprises one or more tabs formed on the inside of each flange, said tabs on each flange being aligned with the corresponding tabs on the opposite flange, said tabs being adapted to engage each other when said body is distended by the pressure applied to said flanges to limit the maximum separation of said tissue clamping jaws.

20. The surgical clip applier of claim 8, wherein each of said clips includes:

jaw guide means formed on said opposite sides of said body for receiving and guiding said clip retaining jaws along said flanges as said clip sleeve is retracted.

21. The surgical clip applier of claim 20, wherein:

said jaw guide means comprises a pair of indentations formed on said opposite sides of said body which extend rearwardly into said flanges and define a pair of ridges extending across the rear of said flanges for engaging said clip retaining jaws; and said clip retaining jaws are adapted to be received in said indentations and guided along said flanges into engagement with said ridges.

22. A surgical clip applier, comprising:

a housing;

an elongated clip sleeve adapted to receive a plurality of surgical clips arranged front to back in a row, said clip sleeve being mounted for longitudinal reciprocating movement relative to said housing;

a pusher mounted on said clip sleeve for engaging the rearmost clip in the row, said pusher being movable one step at a time along said clip sleeve to advance the row of clips toward an open front end of said clip sleeve;

ratchet means operable each time said clip sleeve is reciprocated for advancing said pusher and the row of clips by one step along said clip sleeve, each step corresponding to the length of one clip in the row, said ratchet means including a first ratchet mechanism operable when said clip sleeve is retracted for advancing said pusher and the row of surgical clips by one step relative to said clip sleeve and a second ratchet mechanism operable when said clip sleeve is advanced for advancing said pusher and the row of surgical clips by one step relative to said housing; and means for reciprocating said clip sleeve relative to said housing to advance the row of clips toward said front end of said clip sleeve and to move the frontmost clip in the row outward from said front end of said clip sleeve.

23. The surgical clip applier of claim 22, wherein:

said first ratchet mechanism includes a first pawl formed on said pusher for engaging a plurality of slots formed on said housing; and said second ratchet mechanism includes a second pawl formed on said pusher for engaging a plurality of slots formed on said clip sleeve.

24. The surgical clip applier of claim 23, wherein:

said slots on said housing and said slots on said clip sleeve are uniformly spaced apart by a distance equal to the length occupied by one surgical clip in the row.

* * * * *